United States Patent
Teraoka et al.

(10) Patent No.: US 11,166,701 B2
(45) Date of Patent: *Nov. 9, 2021

(54) ULTRASOUND DIAGNOSTIC SYSTEM

(71) Applicant: General Electric Company, Schenectady, NY (US)

(72) Inventors: Yuri Teraoka, Tokyo (JP); Yuko Shibata, Tokyo (JP); Manabu Arima, Tokyo (JP); Seiji Funaya, Tokyo (JP); Masaru Ogasawara, Tokyo (JP)

(73) Assignee: General Electric Company, Schenectady, NY (US)

( * ) Notice: Subject to any disclaimer, the term of this patent is extended or adjusted under 35 U.S.C. 154(b) by 140 days.

This patent is subject to a terminal disclaimer.

(21) Appl. No.: 16/428,733

(22) Filed: May 31, 2019

(65) Prior Publication Data

US 2019/0365359 A1  Dec. 5, 2019

(30) Foreign Application Priority Data

May 31, 2018  (JP) .............................. JP2018-104746

(51) Int. Cl.
 *A61B 8/00* (2006.01)
 *A61B 8/08* (2006.01)
 *A61B 8/14* (2006.01)

(52) U.S. Cl.
 CPC ............ *A61B 8/565* (2013.01); *A61B 8/4254* (2013.01); *A61B 8/483* (2013.01); *A61B 8/14* (2013.01);

(Continued)

(58) Field of Classification Search
 CPC ....... A61B 8/14; A61B 8/4254; A61B 8/4477; A61B 8/463; A61B 8/466; A61B 8/467;
 (Continued)

(56) References Cited

U.S. PATENT DOCUMENTS

2008/0126306 A1* 5/2008 Corona ............... H04L 41/0853
2012/0278359 A1  11/2012 Igarashi
(Continued)

FOREIGN PATENT DOCUMENTS

JP  2014193193 A  10/2014
JP  2015229069 A  12/2015
(Continued)

OTHER PUBLICATIONS

JP2018-104746 Notice of Allowance dated Jun. 13, 2019 (untranslated).

*Primary Examiner* — Gil H. Lee

(57) ABSTRACT

A system 100 comprises a first medical image capture apparatus UL1 and a second medical image capture apparatus UL2 that share values of at least some of a plurality of preferences and are of different kinds, wherein a first control device 81 in the first ultrasonic diagnostic apparatus UL1 executes an output function of outputting a value of a preference that the first input device 71 has accepted, to a server 104 along with information on the kind of the first ultrasonic diagnostic apparatus UL1, and a server control device 1411 converts the output value of the preference based on conversion information, and then, transmits the converted value to the second ultrasonic diagnostic apparatus UL2. The second ultrasonic diagnostic apparatus UL2 converts the converted value from the server 104 into that in the kind of the second medical image capture apparatus, and performs setting of the converted value.

13 Claims, 23 Drawing Sheets

(52) U.S. Cl.
CPC ............... *A61B 8/463* (2013.01); *A61B 8/466* (2013.01); *A61B 8/5246* (2013.01); *G06T 2207/10136* (2013.01)

(58) Field of Classification Search
CPC ......... A61B 8/483; A61B 8/5246; A61B 8/54; A61B 8/565; A61B 8/585; G06T 2207/10136
See application file for complete search history.

(56) References Cited

U.S. PATENT DOCUMENTS

2014/0278457 A1* 9/2014 Weiler .................. G16H 40/67 705/2
2017/0295447 A1* 10/2017 Tegegne .................. H04W 4/50

FOREIGN PATENT DOCUMENTS

| | | |
|---|---|---|
| JP | 2016022096 A | 2/2016 |
| JP | 2017111471 A | 6/2017 |
| WO | 2012096109 A1 | 7/2012 |
| WO | 2015182478 A1 | 12/2015 |

\* cited by examiner

| VER.1 | FILTER NAME | FILTER 0 | FILTER 1 | FILTER 2 | FILTER 3 | FILTER 4 | FILTER 5 |
|---|---|---|---|---|---|---|---|
| | FUNCTION | f0 | f1 | f2 | f3 | f4 | f5 |

| VER.2 | FILTER NAME | FILTER 0 | FILTER 1 | FILTER 2 | FILTER 3 | FILTER 4 | FILTER 5 | FILTER 6 |
|---|---|---|---|---|---|---|---|---|
| | FUNCTION | f0 | f1 | f6 | f2 | f3 | f4 | f5 |

| VER.3 | FILTER NAME | FILTER 0 | FILTER 1 | FILTER 2 | FILTER 3 | FILTER 4 | FILTER 5 | FILTER 6 | FILTER 7 |
|---|---|---|---|---|---|---|---|---|---|
| | FUNCTION | f0 | f1 | f6 | f2 | f3 | f7 | f4 | f5 |

| VER.2 | VER.1 |
|---|---|
| FILTER 2 (f6) → | FILTER 5 (f5) |
| FILTER 3 → | FILTER 2 |
| FILTER 4 → | FILTER 3 |
| FILTER 5 → | FILTER 4 |
| FILTER 6 → | FILTER 5 |

| VER.3 | VER.1 |
|---|---|
| FILTER 2 (f6) → | FILTER 5 (f5) |
| FILTER 3 → | FILTER 2 |
| FILTER 4 → | FILTER 3 |
| FILTER 5 (f7) → | FILTER 5 (f5) |
| FILTER 6 → | FILTER 4 |
| FILTER 7 → | FILTER 5 |

| ULTRASONIC DIAGNOSTIC APPARATUS 101 | VER.2 |
| ULTRASONIC DIAGNOSTIC APPARATUS 102 | VER.3 |
| ULTRASONIC DIAGNOSTIC APPARATUS 103 | VER.1 |

FIG.21

| ULTRASONIC DIAGNOSTIC APPARATUS 201 | VER.1 |
|---|---|
| ULTRASONIC DIAGNOSTIC APPARATUS 202 | VER.2 |
| ULTRASONIC DIAGNOSTIC APPARATUS 203 | VER.3 |
| ULTRASONIC DIAGNOSTIC APPARATUS 204 | VER.2 |
| ULTRASONIC DIAGNOSTIC APPARATUS 205 | VER.1 |

| ULTRASONIC DIAGNOSTIC APPARATUS 201 | VER.1 | SHARING |
|---|---|---|
| ULTRASONIC DIAGNOSTIC APPARATUS 202 | VER.2 | |
| ULTRASONIC DIAGNOSTIC APPARATUS 203 | VER.3 | |
| ULTRASONIC DIAGNOSTIC APPARATUS 204 | VER.2 | |
| ULTRASONIC DIAGNOSTIC APPARATUS 205 | VER.1 | SHARING |

| INFORMATION A | SHARED OVER ALL VERSIONS | 1ST INFORMATION |
| --- | --- | --- |
| INFORMATION B | SHARED WITHIN ALL OF SAME VERSION | 2nd INFORMATION |
| INFORMATION C | SHARED WITHIN VER.1 | |

ULTRASOUND DIAGNOSTIC SYSTEM

FIELD OF THE INVENTION

The present invention relates to a system in which a plurality of medical image capture apparatuses are connected via a network.

BACKGROUND

A lot of information such as preferences is set in a medical image capture apparatus. For example, such information to be set in an ultrasonic diagnostic apparatus, which is an example of medical image capture apparatuses, includes preferences such as several kinds of imaging conditions for acquiring an ultrasonic image. The information also includes a body pattern, a comment, a cursor for performing measurement, conditions of image reconstruction for obtaining a 3D image or the like.

In most cases, the preferences described above are customized according to the user's purpose and/or preference. In a hospital having a plurality of ultrasonic diagnostic apparatuses, however, there is a need to share values of the preferences for guaranteeing precision of examinations.

Among the plurality of the ultrasonic diagnostic apparatuses, however, there sometimes exist ultrasonic diagnostic apparatuses of different kinds, i.e., those having mutually different values of preferences. In this case, when a value of a preference set for a certain apparatus is set into another apparatus without any modification, a failure or an unexpected behavior of the apparatuses may follow.

BRIEF SUMMARY

One embodiment of the invention made for solving the above problem is a system comprising: a first medical image capture apparatus and a second medical image capture apparatus connected via a network, said first medical image capture apparatus and said second medical image capture apparatus sharing information of at least some of a plurality of preferences set in each of said first and second medical image capture apparatuses, and said first and second medical image capture apparatuses are of different kinds; a storage device; a first control device; and a second control device, wherein said first medical image capture apparatus has: an input device for accepting an input of information of the preference shared with said second medical image capture apparatus; and said first control device configured to output the information of said preference that said input device has accepted, to said network along with information on the kind of said first medical image capture apparatus, said storage device conversion information for converting information of a preference in said first medical image capture apparatus into that in said second medical image capture apparatus, said conversion information being stored according to the kinds of said first and second medical image capture apparatuses, and said second control device is configured to: convert the information of said preference output by said first control device into that in the kind of said second medical image capture apparatus based on the conversion information, said conversion information for said conversion being identified by said information on the kind of said first medical image capture apparatus output by said first control device; and set the information of said preference after being converted, into said second medical image capture apparatus.

Another embodiment of the invention made for solving the above problem is a system comprising: a plurality of medical image capture apparatuses including a plurality of kinds connected via a network, said plurality of medical image capture apparatuses including a fourth medical image capture apparatus and a fifth medical image capture apparatus that share information set and used in each of said plurality of medical image capture apparatuses, and are of the same kind; a storage device in which kind identification information for identifying a kind of each of said plurality of medical image capture apparatuses is stored; a fourth control device; a fifth control device; and a sixth control device, wherein said fourth medical image capture apparatus has: an input device for accepting an input of information set and used in said medical image capture apparatuses; and said fourth control device configured to output the information that said input device has accepted, to said network along with information on the kind of said fourth medical image capture apparatus, said sixth control device is configured to identify a fifth medical image capture apparatus of the same kind as that output by said fourth control device based on said kind identification information and output the information accepted by said input device and output from said fourth control device, to said fifth medical image capture apparatus, and said fifth medical image capture apparatus has said fifth control device, said fifth control device setting the information output by said sixth control device, into said fifth medical image capture apparatus.

According to the one embodiment described above, for the first medical image capture apparatus and second medical image capture apparatus of mutually different kinds, information of a preference input at the first medical image capture apparatus is converted based on the conversion information and set into the second medical image capture apparatus, and thus, a failure or an unexpected behavior of the apparatuses can be prevented from occurring.

According to another embodiment described above, information input at said fourth medical image capture apparatus is set into said fifth medical image capture apparatus that is identified as being of the same kind as said fourth medical image capture apparatus. Since the information is thus set into the medical image capture apparatus of the same kind, a failure or an unexpected behavior of the apparatuses can be prevented from occurring.

BRIEF DESCRIPTION OF THE DRAWINGS

FIG. 5 is a diagram showing an example of information on image filters.

FIG. 6 is a diagram showing another example of the information on image filters.

FIG. 7 is a diagram showing another example of the information on image filters.

FIG. 8 is a diagram showing an example of first conversion information.

FIG. 9 is a diagram showing an example of the first conversion information.

FIG. 21 is a diagram showing the version information in the second embodiment.

FIG. 25 is a diagram showing an example of sharing apparatus identification information.

DETAILED DESCRIPTION

Now several embodiments of the present invention will be described referring to the accompanying drawings. In the following embodiments, the medical image capture apparatus in the present invention is exemplified by an ultrasonic diagnostic apparatus.

Figure 1:
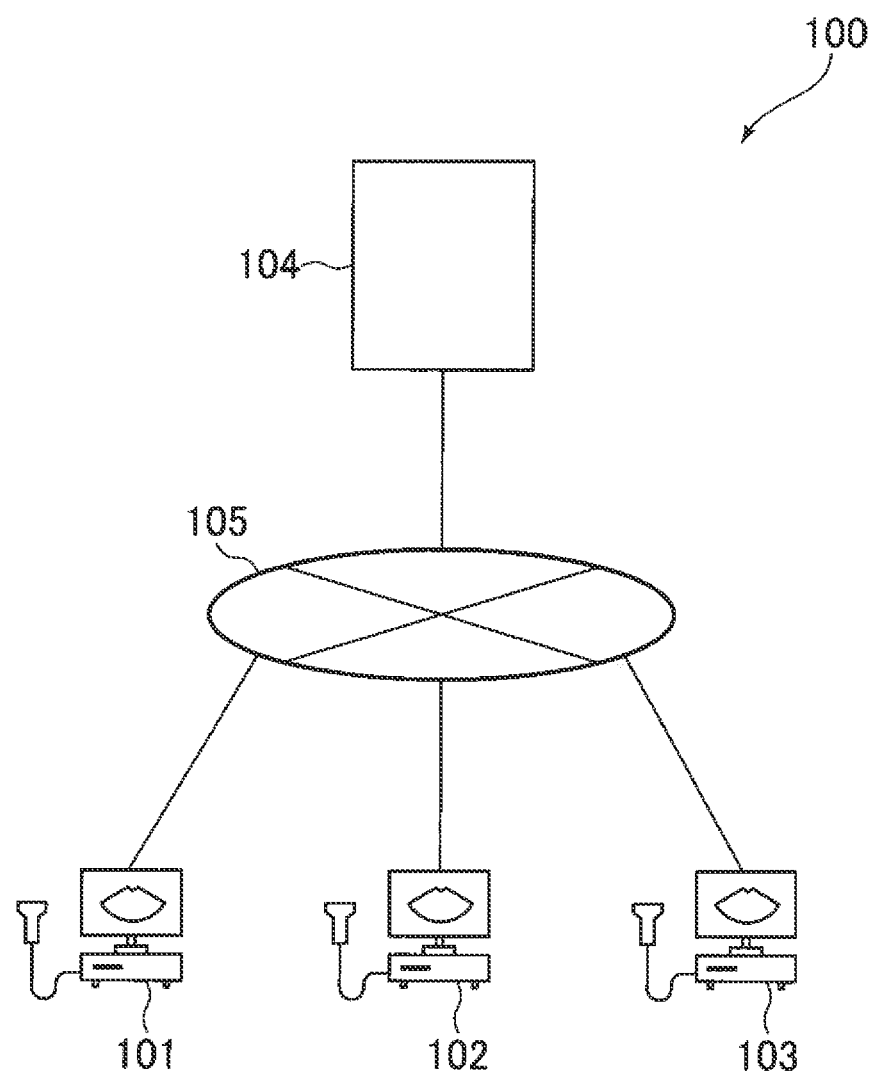
FIG. 1 is a block diagram showing the overall configuration of a system in a first embodiment of the present invention.

To begin with, a first embodiment will be described. A system 100 shown in FIG. 1 comprises a plurality of ultrasonic diagnostic apparatuses 101, 102, 103, and a server 104. The plurality of ultrasonic diagnostic apparatuses 101, 102, 103 are connected with one another via a network 105. The plurality of ultrasonic diagnostic apparatuses 101, 102, 103 are also each connected with the server 104 via the network 105.

Figure 2:
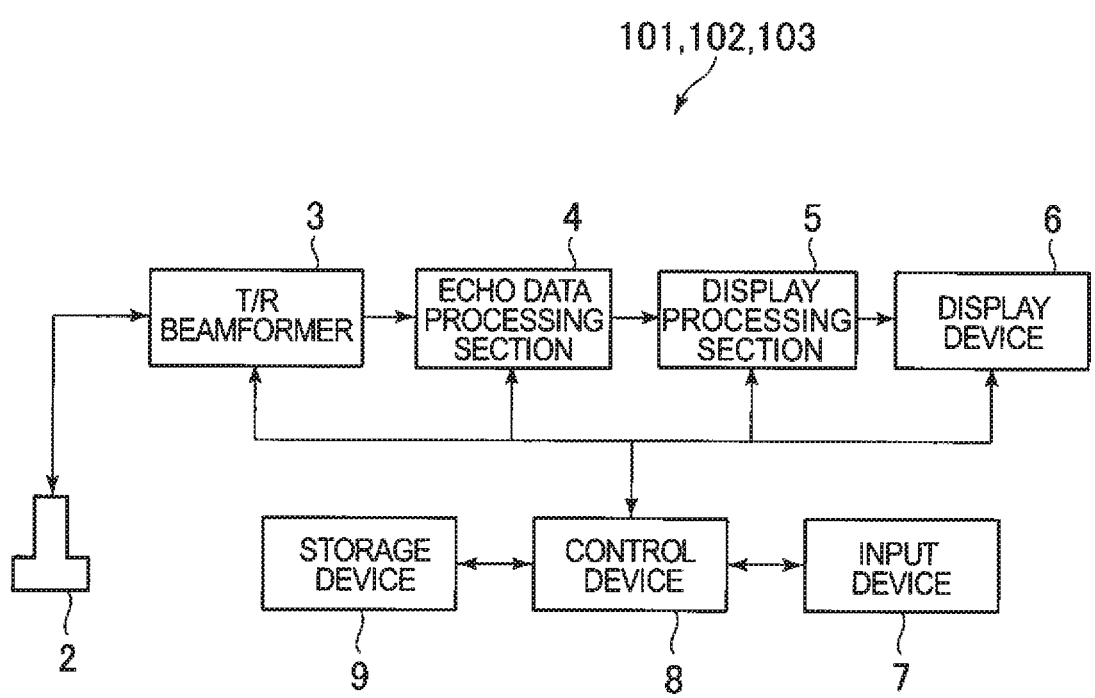
FIG. 2 is a block diagram showing a configuration of an ultrasonic diagnostic apparatus constituting the system shown in FIG. 1.

As shown in FIG. 2, the ultrasonic diagnostic apparatuses 101, 102, 103 each comprise an ultrasonic probe 2, a transmission/reception (T/R) beamformer 3, an echo data processing section 4, a display processing section 5, a display device 6, an input device 7, a control device 8, and a storage device 9.

The ultrasonic probe 2 transmits ultrasound and receives its echo signals to/from a biological tissue in a subject to be examined. The T/R beamformer 3 drives the ultrasonic probe 2 to transmit ultrasound having predetermined transmission conditions based on control signals from the control device 8. The T/R beamformer 3 also applies signal processing, such as phased addition processing, to echo signals of the ultrasound.

The echo data processing section 4 applies processing for producing an ultrasonic image to echo data output from the T/R beamformer 3. For example, the echo data processing section 4 applies B-mode processing including logarithm compression processing, envelope detection processing, etc. to create B-mode data.

The display processing section 5 scan-converts raw data from the echo data processing section 4 by a scan converter to create image data. The display processing section 5 scan-converts the B-mode data, for example, to create B-mode image data. The display processing section 5 also causes an ultrasonic image based on the image data to be displayed on the display device 6. The display processing section 5 causes, for example, a B-mode image based on the B-mode image data to be displayed on the display device 6.

The display device 6 is an LCD (Liquid Crystal Display), an organic EL (Electro-Luminescence) display or the like.

The input device 7 is a device for accepting a user's input of commands and information. The input device 7 is configured to comprise buttons and a keyboard for accepting an operator's input of commands and information, and to further comprise a pointing device, such as a trackball.

The control device 8 is circuitry for controlling the ultrasonic diagnostic apparatus 101, 102, 103, and is a processor, such as, for example, a CPU (Central Processing Unit). The control device 8 loads programs stored in the storage device 9 to control several sections in the ultrasonic diagnostic apparatus 1. The control device 9 is an exemplary embodiment of the control device in the present invention.

For example, the control device 8 loads programs stored in the storage device 9, and causes the functions of the T/R beamformer 3, echo data processing section 4, and display processing section 5 described above to be executed according to the loaded programs. The control device 8 may execute all of the functions of the T/R beamformer 3, all of the functions of the echo data processing section 4, and all of the functions of the display processing section 5 according to the programs, or may execute only some of the functions according to the programs. In the case that only some of the functions are executed according to the programs, the rest of the functions may be executed by hardware such as circuitry.

The control device 8 may also execute functions other than those of the T/R beamformer 3, echo data processing section 4, and display processing section 5 according to programs stored in the storage device 8. This will be discussed in detail later.

The storage device 9 includes non-transitory storage media and transitory storage media. The non-transitory storage media are non-volatile storage media such as, for example, HDD (Hard Disk Drive) and ROM (Read Only Memory). The non-transitory storage media may include portable storage media such as CDs (Compact Disks) and DVDs (Digital Versatile Disks). Programs to be executed by the control device 8 are stored in non-transitory storage media.

The transitory storage media are volatile storage media, such as RAM (Random Access Memory).

In each of the plurality of ultrasonic diagnostic apparatuses 101, 102, 103, information including a plurality of preferences is set. The information is used in each of the plurality of ultrasonic diagnostic apparatuses 101, 102, 103. Specifically, the information includes, in each of the plurality of ultrasonic diagnostic apparatuses 101, 102, 103, imaging conditions for acquiring an ultrasonic image, information given to the ultrasonic image, information used for performing measurement in the ultrasonic image, and reconstruction conditions for performing image reconstruction based on data of the ultrasonic image. Note that the information are not limited thereto.

The imaging conditions include, for example, a gain value, a focal point depth, an image filter, and a contrast value. The imaging conditions may be set for each of a plurality of body parts in the subject. In this case, imaging conditions for each of the plurality of body parts constitute a respective different information or different preference.

The information given to an ultrasonic image includes, for example, a comment provided to the ultrasonic image, and a body pattern. The information used for performing measurement in the ultrasonic image include, for example, a cursor displayed on the ultrasonic image for performing measurement, and a calculation formula. The reconstruction conditions for performing image reconstruction based on data of the ultrasonic images include, for example, reconstruction conditions for producing a 3D or 4D image.

Among the plurality of ultrasonic diagnostic apparatuses 101, 102, 103, those sharing at least some of the plurality of preferences and being of different kinds will be referred to herein as a first ultrasonic diagnostic apparatus UL1 and a second ultrasonic diagnostic apparatus UL2. The kinds include, for example, the version of the ultrasonic diagnostic apparatus, or the purpose of the ultrasonic diagnostic apparatus, such as an obstetric purpose or a general purpose. The version represents, for example, a history of revision of the specification of an ultrasonic diagnostic apparatus.

Figure 3:
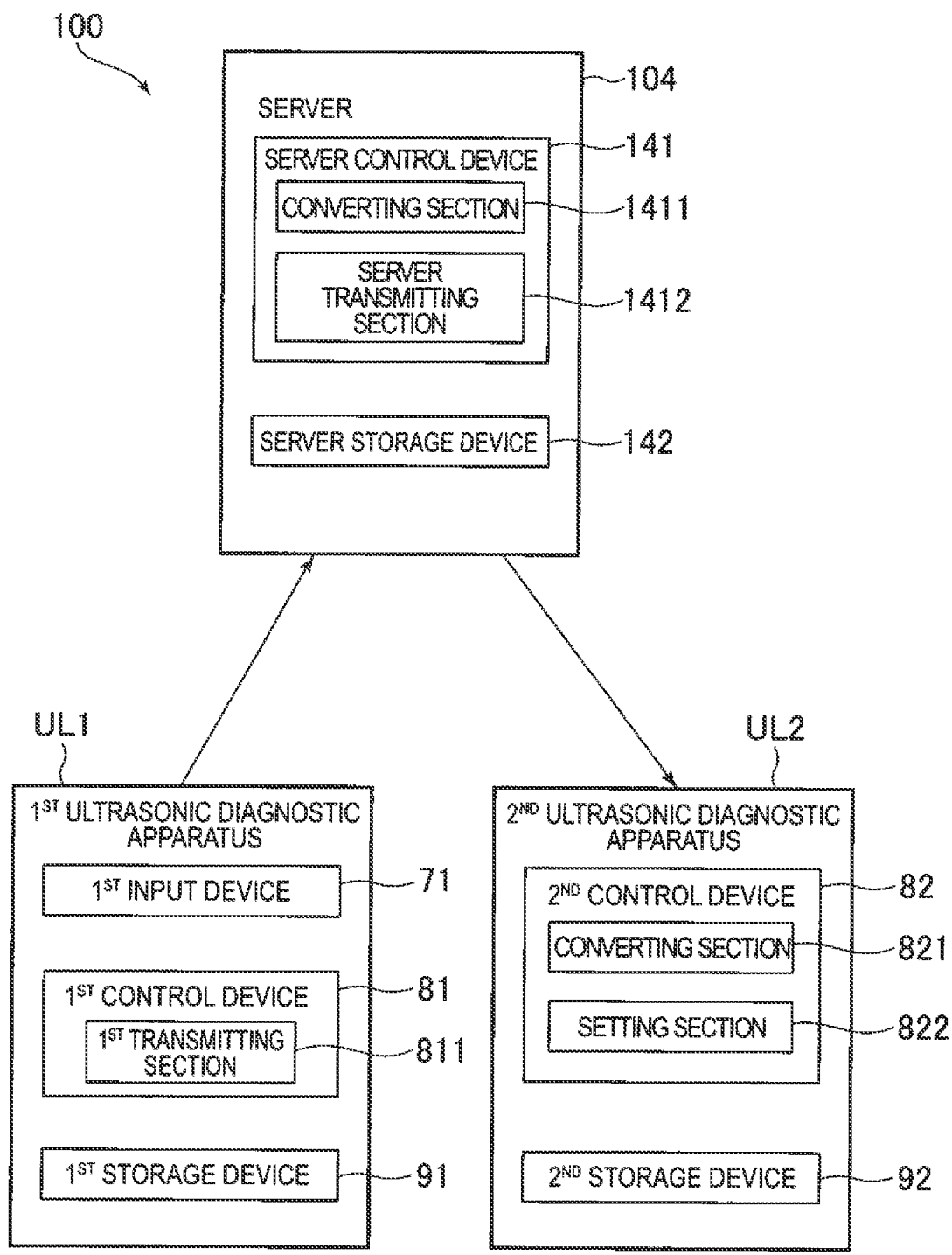
FIG. 3 is a block diagram showing a first ultrasonic diagnostic apparatus, a second ultrasonic diagnostic apparatus, and a server in the first embodiment.

FIG. 3 shows the first ultrasonic diagnostic apparatus UL1 and second ultrasonic diagnostic apparatus UL2. The first ultrasonic diagnostic apparatus UL1 is one of the plurality of ultrasonic diagnostic apparatuses 101, 102, 103 at which an input of information of a preference is performed. For example, the information of the preference includes imaging conditions for acquiring an ultrasonic image. Any one of the ultrasonic diagnostic apparatuses 101, 102, 103 may serve as the first ultrasonic diagnostic apparatus UL1. The second ultrasonic diagnostic apparatus UL2 is one of the plurality of ultrasonic diagnostic apparatuses 101, 102, 103 into which the information of the preference input at the first ultrasonic diagnostic apparatus UL1 is set. Any one of the ultrasonic diagnostic apparatuses 101, 102, 103 may serve as the second ultrasonic diagnostic apparatus UL2.

As shown in FIG. 3, the input device 7, control device 8, and storage device 9 in the first ultrasonic diagnostic apparatus UL1 are designated herein as a first input device 71, a first control device 81, and a first storage device 91, respectively. Moreover, as shown in FIG. 3, the control device 8 and storage device 9 in the second ultrasonic diagnostic apparatus UL2 are designated herein as a second control device 82 and a second storage device 92, respectively. Note that in FIG. 3 are shown only part of the components of the ultrasonic diagnostic apparatus shown in FIG. 2.

The first input device 71 is an exemplary embodiment of the input device in the present invention. The first control device 81 loads a program stored in the first storage device 91, and causes the function of the first transmitting section 811 to be executed according to the program. The function of the first transmitting section 811 will be discussed later. The function of the first transmitting section 811 is an exemplary embodiment of the output function in the present invention. The first control device 81 is an exemplary embodiment of the first control device in the present invention.

The second control device 82 loads programs stored in the second storage device 92, and causes the functions of a converting section 821 and a setting section 822 to be executed according to the programs. The functions of the converting section 821 and setting section 822 will be discussed later. The function of the converting section 821 is an exemplary embodiment of the converting function in the present invention. The function of the setting section 822 is an exemplary embodiment of the setting function in the present invention. The second control device 82 is an exemplary embodiment of the second control device in the present invention.

In the second storage device 92 is stored second conversion information. Details thereof will be discussed later. The second storage device is an exemplary embodiment of the storage device in the present invention.

Information of a preference input at the first ultrasonic diagnostic apparatus UL1 is input to the server 104 via the network 105 (not shown in FIG. 3), is subjected to conversion at the server 104, and is input from the server 104 to the second ultrasonic diagnostic apparatus UL2 via the network 105.

The server 104 has a server control device 141 and a server storage device 142. The server control device 141 loads programs stored in the server storage device 142, and causes the functions of a converting section 1411 and a server transmitting section 1412 according to the programs. The functions of the converting section 1411 and server transmitting section 1412 will be discussed later. The server control device 141 is an exemplary embodiment of the second control device in the present invention.

In the server storage device 142 is stored first conversion information. Details thereof will be discussed later. The first conversion information and the aforementioned second conversion information constitute exemplary embodiments of the conversion information in the present invention. The server storage device 142 is an exemplary embodiment of the storage device in the present invention.

Figure 4:
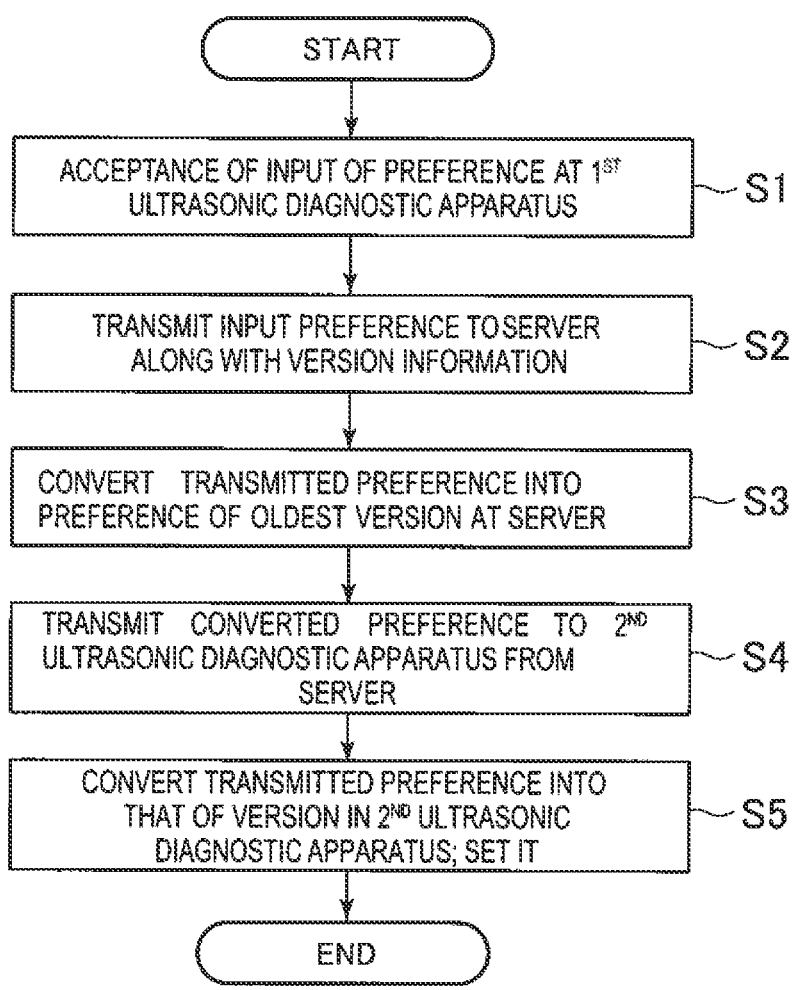
FIG. 4 is a flow chart showing an operation of the first embodiment.

Next, an operation of the present embodiment will be described based on the flow chart in FIG. 4. The flow chart in FIG. 4 is a flow representing the processing when setting information of a preference input at the first ultrasonic diagnostic apparatus UL1 as information of the preference in the second ultrasonic diagnostic apparatus UL2.

First, at Step S1, the first input device 71 in the first ultrasonic diagnostic apparatus UL1 accepts an operator's input of information of a preference. The information of the preference input here is one to be shared among the ultrasonic diagnostic apparatuses 101, 102, 103. In the present embodiment, the first input device 71 accepts as information of a preference an input of, for example, selecting one of a plurality of image filters as an image filter to be used in ultrasonic image production. The plurality of image filters will be described in FIG. 5 to FIG. 7 below. The value input at Step S1 is stored in the first storage device 91.

Next, at Step S2, the first transmitting section 811 transmits the information of the preference input at Step S1 to the server 104 via the network 105. The first transmitting section 811 transmits the information of said preference to said server 104 along with information on the kind of the one (corresponding to the first ultrasonic diagnostic apparatus UL1) of the plurality of ultrasonic diagnostic apparatuses 101, 102, 103 at which the input of the information of the preference is performed at Step S1. In the present embodiment, it is assumed that the input of the information of the preference is performed at the ultrasonic diagnostic apparatus 101. That is, the first ultrasonic diagnostic apparatus UL1 is the ultrasonic diagnostic apparatus 101.

The information on the kind is stored in the first storage device 91 in the first ultrasonic diagnostic apparatus UL1. In the present embodiment, the information on the kind is information on the version of an ultrasonic diagnostic apparatus. For example, the ultrasonic diagnostic apparatus 101 is in version 2 (Ver. 2), the ultrasonic diagnostic apparatus 102 is in version 3 (Ver. 3), and the ultrasonic diagnostic apparatus 103 is in version 1 (Ver. 1). A larger one of the version numbers 1 to 3 indicates that the ultrasonic diagnostic apparatus is in a version later in time.

As described earlier, in the present embodiment, the input of the information of the preference is performed at the ultrasonic diagnostic apparatus 101, and accordingly, the information on the kind transmitted by the first transmitting section 811 is information representing version 2.

Next, at Step S3, the information of the preference and information representing version 2 transmitted at Step S2 is input to the server 104. The converting section 1411 then performs conversion on the information of the preference input to the server 104. Here, conversion into an oldest one of the versions of the second ultrasonic diagnostic apparatus UL2 is performed. The oldest version is version 1.

Now details of the conversion processing by the converting section 1411 will be particularly described. In the present embodiment, at Step S1 described above, the information of the preference input at the ultrasonic diagnostic apparatus 101 is an image filter. Here, in the storage device 9 in each of the ultrasonic diagnostic apparatuses 101, 102, 103 are stored a plurality of image filters. Exemplary image filters in each of the ultrasonic diagnostic apparatuses 101, 102, 103 are shown in FIGS. 5 to 7. The information on an image filter includes a filter name of the image filter and a mathematical function for the image filter under the filter name. The filter name corresponds to formal information of the preference. The mathematical function of the image filter corresponds to substantial information of the preference.

In FIG. 5 is shown information If1 on image filters stored in the storage device 9 of the ultrasonic diagnostic apparatus 103 in version 1. The image filter information If1 includes filter names "Filter 0" to "Filter 5," and "Mathematical function f0" to "Mathematical function f5," which are mathematical functions for the image filters under those filter names.

In FIG. 6 is shown information If2 on image filters stored in the storage device 9 of the ultrasonic diagnostic apparatus 101 in version 2. The image filter information If2 includes filter names "Filter 0" to "Filter 6," and "Mathematical function f0" to "Mathematical function f6," which are mathematical functions for the image filters under those filter names.

In FIG. 7 is shown information If3 on image filters stored in the storage device 9 of the ultrasonic diagnostic apparatus 102 in version 3. The image filter information If3 includes filter names "Filter 0" to "Filter 7," and "Mathematical function f0" to "Mathematical function f7," which are mathematical functions for the image filters under those filter names.

Combinations of filter names and mathematical functions for the image filters in the image filter information If2 include different combinations from those in the image filter information If1. Specifically, there exists the mathematical function f6 in the image filter information If2 between the mathematical functions f1 and f2 that does not exist in the image filter information If1, so that the combinations of filter names and mathematical functions after Filter 2 are different between the image filter information If1 and the image filter information If2.

Moreover, combinations of filter names and mathematical functions for the image filters in the image filter information If3 include different combinations from those in the image filter information If2. Specifically, there exists the mathematical function f7 in the image filter information If3 between the mathematical functions f3 and f4 that does not exist in the image filter information If2, so that the combinations of filter names and mathematical functions after Filter 5 are different between the image filter information If2 and the image filter information If3.

Likewise, combinations of filter names and mathematical functions for the image filters in the image filter information If3 include different combinations from those in the image filter information If1.

In the server storage device 142 in the server 104 are stored first conversion information Ic1A, Ic1B shown in FIGS. 8 and 9. The first conversion information Ic1A, Ic1B are information on conversion into filter names and mathematical functions in one of the second ultrasonic diagnostic apparatuses UL2 that is in the oldest version.

Specifically, the first conversion information Ic1A is information for converting a filter name and a mathematical function in the ultrasonic diagnostic apparatus 101 in version 2 into those in the ultrasonic diagnostic apparatus 103 in version 1. That is, the first conversion information Ic1A is information for converting formal information and substantial information of a preference in the version of the ultrasonic diagnostic apparatus 101 into those in the version of the ultrasonic diagnostic apparatus 103. The first conversion information Ic1A is also information on conversion on the filter name for filters having the same filter name but different mathematical functions between the ultrasonic diagnostic apparatus 101 and ultrasonic diagnostic apparatus 103. The filter names for filters having the same filter name and the same mathematical function between the ultrasonic diagnostic apparatus 101 and ultrasonic diagnostic apparatus 103 is not included in the first conversion information Ic1A because the converting section 1411 does not perform conversion between them.

Among the mathematical functions f1 to f6 in the ultrasonic diagnostic apparatus 101, the mathematical function f6 that does not exist in the ultrasonic diagnostic apparatus 103 is defined in the first conversion information Ic1A so that it is converted into one of the mathematical functions f1 to f5 in the ultrasonic diagnostic apparatus 103 by which image quality closest to that obtained using the mathematical function f6 can be attained. In the present embodiment, image quality obtained using the mathematical function f6 is closest to that obtained using the mathematical function f5, and accordingly, the first conversion information Ic1A is defined so that the filter name "Filter 2" is converted into the filter name "Filter 5" and the mathematical function f6 is converted into the mathematical function f5.

The first conversion information Ic1B is information for converting a filter name and a mathematical function in the ultrasonic diagnostic apparatus 102 in version 3 into those in the ultrasonic diagnostic apparatus 103 in version 1. That is, the first conversion information Ic1B is information for converting formal information and substantial information of a preference in the version of the ultrasonic diagnostic apparatus 102 into those in the version of the ultrasonic diagnostic apparatus 103. The first conversion information Ic1B is information on conversion on the filter name for filters having the same filter name but different mathematical functions between the ultrasonic diagnostic apparatus 102 and ultrasonic diagnostic apparatus 103. The filter name for a filter having the same filter name and the same mathematical function between the ultrasonic diagnostic apparatus 102 and ultrasonic diagnostic apparatus 103 is not included in the first conversion information Ic1B because the converting section 1411 does not perform conversion between them.

Among the mathematical functions f1 to f7 in the ultrasonic diagnostic apparatus 102, the mathematical functions f6, f7 that do not exist in the ultrasonic diagnostic apparatus 103 are defined in the first conversion information Ic1B so that they are converted into ones of the mathematical functions f1 to f5 in the ultrasonic diagnostic apparatus 103 by which image quality closest to that obtained using the mathematical functions f6, f7 can be attained. In the present embodiment, image quality obtained using the mathematical function f6 is closest to that obtained using the mathematical function f5, and accordingly, the first conversion information Ic1B is defined so that the filter name "Filter 2" is converted into the filter name "Filter 5" and the mathematical function f6 is converted into the mathematical function f5. Similarly, image quality obtained using the mathematical function f7 is closest to that obtained using the mathematical function f5, and accordingly, the first conversion information Ic1B is defined so that the mathematical function f7 is converted into the mathematical function f5. The filter name for the mathematical function f7, however, is the same as that for the mathematical function f5 in the ultrasonic diagnostic apparatus 103, which is Filter 5, and accordingly, conversion on the filter name does not have to be defined in the first conversion information Ic1B.

The first conversion information Ic1A, Ic1B are each an exemplary embodiment of the first conversion information in the present invention. The filter names for the ultrasonic diagnostic apparatus 103 in the first conversion information Ic1A, Ic1B are each an exemplary embodiment of the third value in the present invention.

In the present embodiment, the converting section 1411 performs conversion using the first conversion information Ic1A because the information on the kind input to the server 104 is information as version 2. For example, in the case that an input for selecting Filter 6 is performed at Step S1, the converting section 1411 converts "Image filter 6" into "Image filter 5" using the first conversion information Ic1A.

Here, in the case that Filter 6 chosen in the ultrasonic diagnostic apparatus 101 is set into the ultrasonic diagnostic apparatuses 102, 103 as well, the value (mathematical function f4) for Filter 6 in the ultrasonic diagnostic apparatus 102 is different from that in the ultrasonic diagnostic apparatus 101. On the other hand, while in the ultrasonic diagnostic apparatus 103 the same mathematical function as the mathematical function f5 for Filter 6 in the ultrasonic diagnostic apparatus 101 exists, the filter name "Filter 6" does not exist. Thus, since different combinations of filter names and mathematical functions between ultrasonic diagnostic apparatuses in different versions sometimes have different information of preferences, conversion processing is required when setting Filter 6 selected in the ultrasonic diagnostic apparatus 101 into the ultrasonic diagnostic apparatuses 102, 103 as well.

Once conversion on the information of the preference has been performed at Step S3, the server transmitting section 1412 transmits the converted information of the preference to the second ultrasonic diagnostic apparatus UL2 via the network 105 (not shown in FIG. 3) at Step S4. The second ultrasonic diagnostic apparatus UL2 designates the ultrasonic diagnostic apparatuses 102, 103, and the information representing "Image filter 5," which is the filter name, is transmitted to them.

Figure 10:
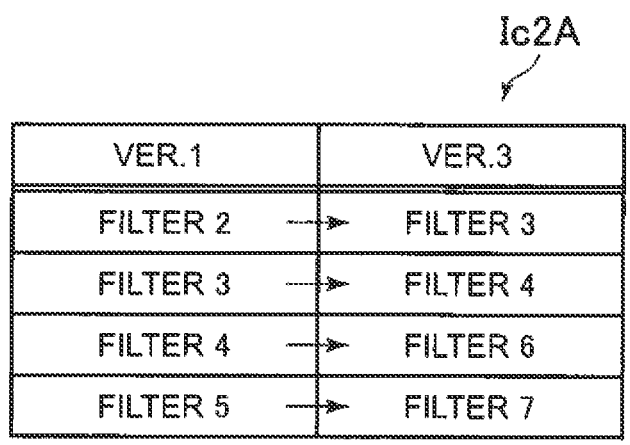
FIG. 10 is a diagram showing an example of second conversion information.

At Step S5, the second ultrasonic diagnostic apparatus UL2 converts the information representing "Image filter 5," which is the filter name, that the server transmitting section 1412 has transmitted, into that in the version of the second ultrasonic diagnostic apparatus as needed. Specifically, the converting section 821 in the ultrasonic diagnostic apparatus 102 performs conversion based on second conversion information Ic2A shown in FIG. 10.

The second conversion information Ic2A is information for converting the information of the preference for the ultrasonic diagnostic apparatus in the oldest version into that in the version of the second ultrasonic diagnostic apparatus UL2. Specifically, the second conversion information Ic2A is information for converting the filter name in version 1 into that in version 3. That is, in the present embodiment, the second conversion information Ic2A is information for converting the formal information of the preference in the version of the ultrasonic diagnostic apparatus 103 into that in the version of the ultrasonic diagnostic apparatus 102. The second conversion information Ic2A is an exemplary embodiment of the second conversion information in the present invention.

In the present embodiment, the converting section 821 converts the filter name "Filter 5" into the filter name "Filter 7" using the second conversion information Ic2A. Then, the setting section 822 performs setting of the image filter by storing into the second storage device 92 the filter name "Filter 7" and mathematical function f5 as the image filter to be used in the ultrasonic diagnostic apparatus 102.

On the other hand, in the present embodiment, the ultrasonic diagnostic apparatus 103 is in version 1 into which the conversion has been performed at the server 104, and accordingly, no conversion occurs in the ultrasonic diagnostic apparatus 103. In the ultrasonic diagnostic apparatus 103, the setting section 822 performs setting of the image filter by storing into the second storage device 92 the filter name "Image filter 5" and mathematical function f5 as the image filter to be used in the ultrasonic diagnostic apparatus 103.

According to the present embodiment described above, even when the ultrasonic diagnostic apparatus 101 and the ultrasonic diagnostic apparatuses 102, 103 have different versions, an image filter having the same mathematical function as that for an image filter selected at the ultrasonic diagnostic apparatus 101 can be set into the ultrasonic diagnostic apparatuses 102, 103 as well. Thus, a failure or an unexpected behavior of the apparatuses can be prevented from occurring.

Figure 11:
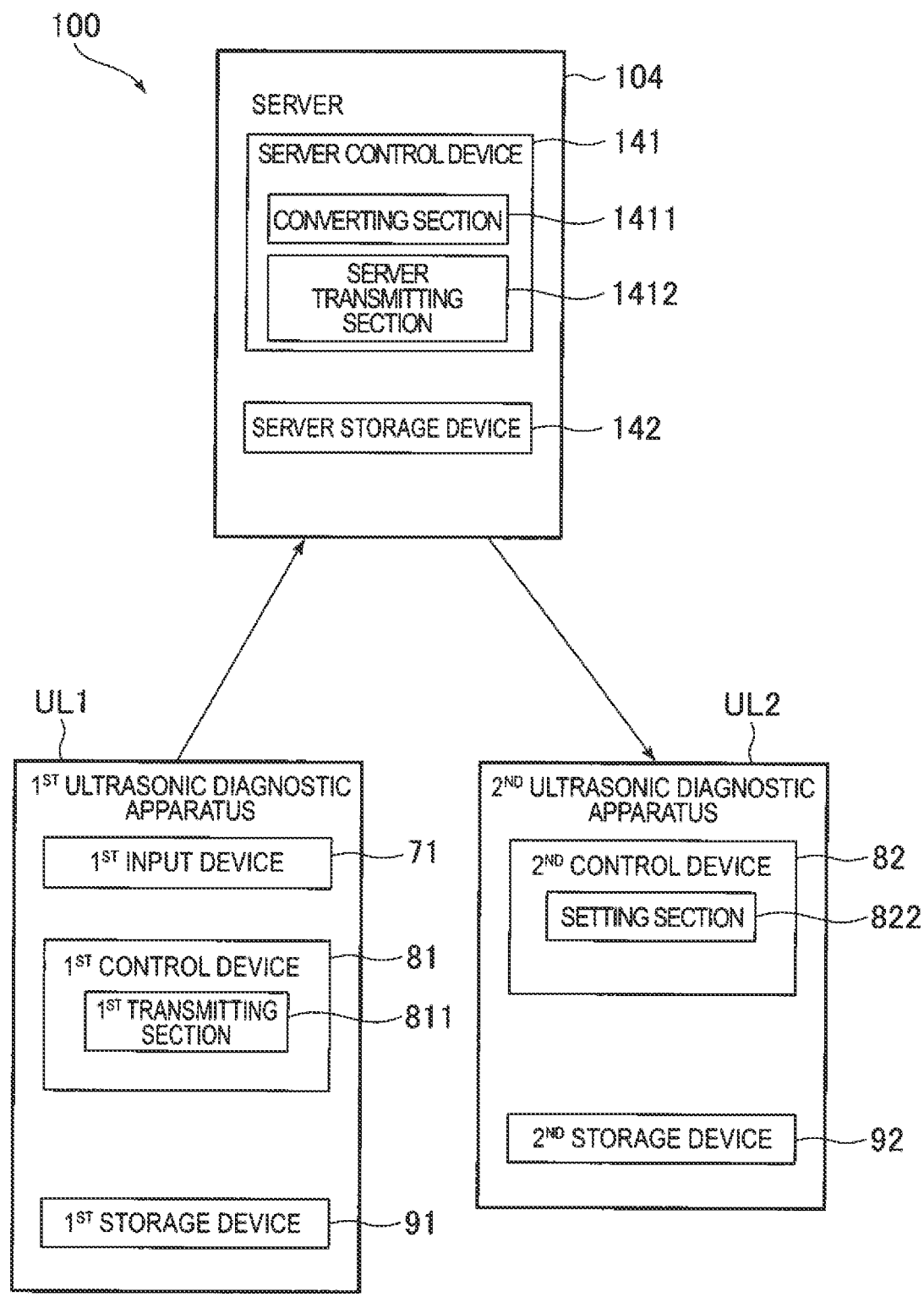
FIG. 11 is a block diagram showing the first ultrasonic diagnostic apparatus, second ultrasonic diagnostic apparatus, and server in a first variation of the first embodiment.

Next, variations of the first embodiment will be described. To begin with, a first variation will be described. As shown in FIG. 11, the second ultrasonic diagnostic apparatus UL2 in a system 100 in the first variation does not have the converting section 821. In the present variation, conversion into all versions is performed by the converting section 1411 in the server 104.

Figure 12:
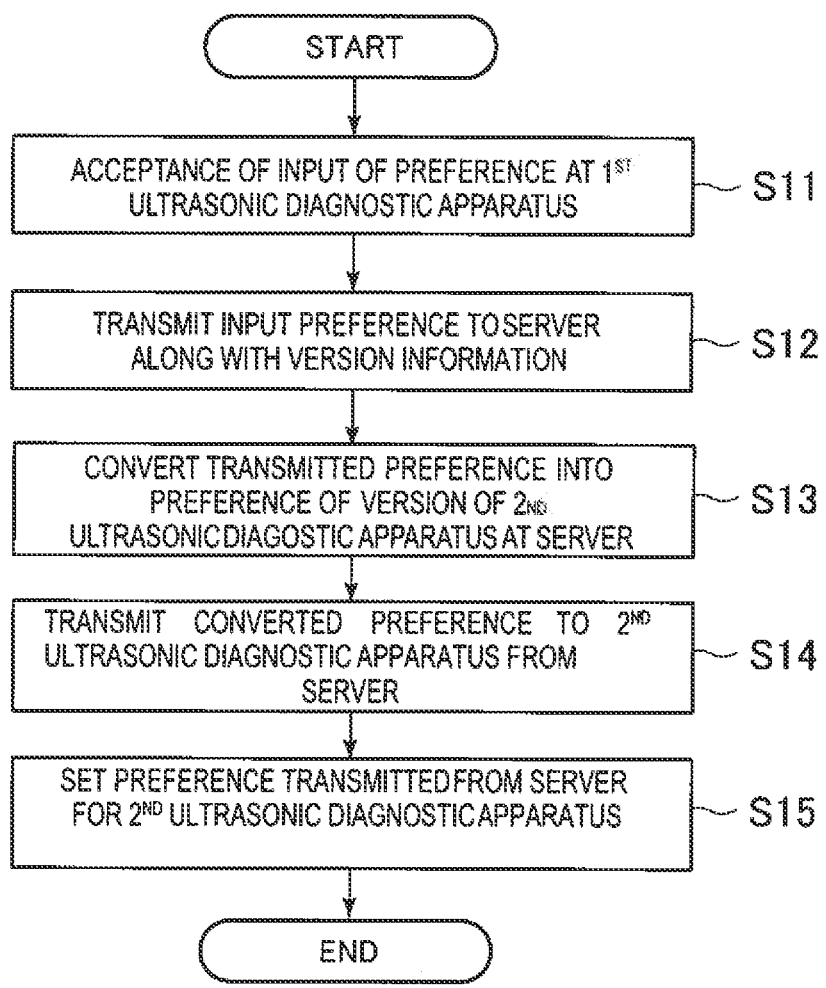
FIG. 12 is a flow chart showing an operation of the first variation of the first embodiment.

Now conversion in the first variation will be specifically described based on the flow chart in FIG. 12. Steps S11, S12 are similar to Steps S1, S2 in FIG. 4, description of which will be omitted. In the present variation, again, it is assumed that an input for selecting an image filter is performed at the ultrasonic diagnostic apparatus 101.

At Step S13, information of a preference and information representing version 2 transmitted at Step S12 are input to the server 104, as in Step S3. The converting section 1411 then performs conversion on the information of the preference input to the server 104. Here, conversion from version 2 to versions 1 and 3 is performed.

Now details will be described. In the server storage device 142 of the server 104 are stored conversion information IcD to IcF shown in FIGS. 13 to 15. The conversion information IcD is information on mutual conversion between a filter name and a mathematical function for the ultrasonic diagnostic apparatus 103 in version 1 and those for the ultrasonic diagnostic apparatus 101 in version 2. The conversion information IcE is information on mutual conversion between a filter name and a mathematical function for the ultrasonic diagnostic apparatus 101 in version 2 and those for the ultrasonic diagnostic apparatus 102 in version 3. Note that the information for Filter 5 for the ultrasonic diagnostic apparatus 102 indicated by a unidirectional arrow in FIG. 14 is for converting the filter name in the ultrasonic diagnostic apparatus 102 into that in the ultrasonic diagnostic apparatus 101, instead of information on mutual conversion between the ultrasonic diagnostic apparatuses 101, 102. The conversion information IcF is information on mutual conversion between the filter name and mathematical function for the ultrasonic diagnostic apparatus 103 in version 1 and those for the ultrasonic diagnostic apparatus 102 in version 3. Note that the information for Filters 2 and 5 for the ultrasonic diagnostic apparatus 102 indicated by unidirectional arrows in FIG. 15 is for converting the filter name in the ultrasonic diagnostic apparatus 102 into that in the ultrasonic diagnostic apparatus 103, instead of information on mutual conversion.

The conversion information IcD to IcF are each an exemplary embodiment of the conversion information in the present invention.

Since in the present variation, the information on the kind input to the server 104 is information in version 2, the converting section 1411 performs conversion using the conversion information IcD, IcE. For example, in the case that an input for selecting Image filter 6 is performed at Step S11, the converting section 1411 converts "Image filter 6" into "Image filter 5" using the conversion information IcD, and "Image filter 6" into "Image filter 7" using the conversion information IcE.

Next, at Step S14, the server transmitting section 1412 transmits the information of the preference converted at Step S13 to the second ultrasonic diagnostic apparatus UL2 via the network 105 (not shown in FIG. 11). The second ultrasonic diagnostic apparatus UL2 designates the ultrasonic diagnostic apparatuses 102, 103. The server transmitting section 1412 transmits information on the image filter according to the versions of the ultrasonic diagnostic apparatuses 102, 103 to them. The server transmitting section 1412 performs the transmission based on version identification information Iv for identifying the versions of the ultrasonic diagnostic apparatuses 101, 102, 103 shown in FIG. 16.

The version identification information Iv is stored in the server storage device 142. Since in the present variation, the ultrasonic diagnostic apparatuses 102, 103 serve as the second ultrasonic diagnostic apparatus UL2, the information Iv on the version contains information on the version of the second ultrasonic diagnostic apparatus UL2. Therefore, the version identification information Iv is an exemplary embodiment of the kind identification information for identifying the kind of the second medical image capture apparatus in the present invention. It will be easily recognized that the ultrasonic diagnostic apparatus 102 or 103 may serve as the first ultrasonic diagnostic apparatus UL1 and the ultrasonic diagnostic apparatus 101 may serve as the second ultrasonic diagnostic apparatus UL2.

The server transmitting section 1412 identifies an ultrasonic diagnostic apparatus to which an image filter according to the version is to be transmitted, based on the version identification information Iv. Specifically, the server transmitting section 1412 transmits the information representing "Image filter 5" converted into version 1 at Step S13, to the ultrasonic diagnostic apparatus 103 in version 1 via the network 105 based on the version identification information Iv. The server transmitting section 1412 also transmits the information representing "Image filter 7" converted into version 3 at Step S13, to the ultrasonic diagnostic apparatus 102 in version 3 via the network 105 based on the version identification information Iv.

Next, at Step S15, the setting section 822 in the ultrasonic diagnostic apparatus 103 serving as the second ultrasonic diagnostic apparatus UL2 performs setting of the image filter by storing into the second storage device 92 "Image filter 5" and its mathematical function f5 transmitted from the server 104 as the image filter to be used in the ultrasonic diagnostic apparatus 103. Similarly, the setting section 822 in the ultrasonic diagnostic apparatus 102 serving as the second ultrasonic diagnostic apparatus UL2 performs setting of the image filter by storing into the second storage device 92 "Image filter 7" and its mathematical function f5 transmitted from the server 104 as the image filter to be used in the ultrasonic diagnostic apparatus 102.

Figure 17:
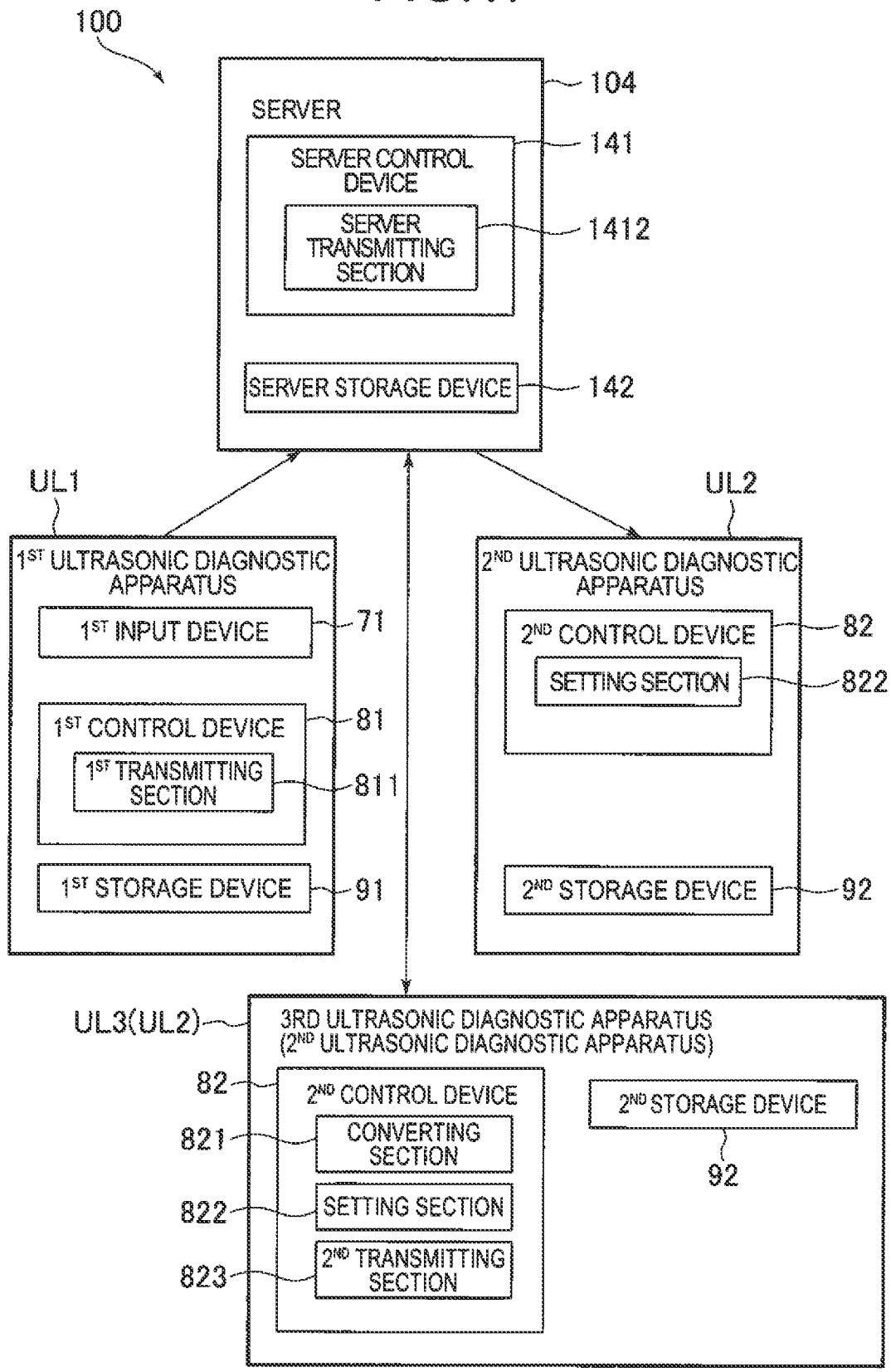
FIG. 17 is a block diagram showing the first ultrasonic diagnostic apparatus, second ultrasonic diagnostic apparatus, a third ultrasonic diagnostic apparatus, and the server in a second variation of the first embodiment.

Next, a second variation will be described. As shown in FIG. 17, the system 100 in the second variation has a third ultrasonic diagnostic apparatus UL3. However, since the third ultrasonic diagnostic apparatus UL3 is an ultrasonic diagnostic apparatus that shares information of preferences set in the first ultrasonic diagnostic apparatus UL1, it also corresponds to the second ultrasonic diagnostic apparatus UL2. The third ultrasonic diagnostic apparatus UL3 is one of the second ultrasonic diagnostic apparatuses UL2 for performing conversion of information of preferences, as will be described below.

The third ultrasonic diagnostic apparatus UL3 comprises a second control device 82 having a converting section 821, a setting section 822, and a second transmitting section 823, and a second storage device 92. In the present variation, conversion into all versions is achieved by the converting section 821 in the third ultrasonic diagnostic apparatus UL3, as will be discussed below. The second control device 82 in the third ultrasonic diagnostic apparatus UL3 is an exemplary embodiment of the second control device in the present invention. A transmitting function by the second transmitting section 823 in the third ultrasonic diagnostic apparatus UL3 is an exemplary embodiment of the transmitting function the second control device executes in the present invention.

While in the present variation the second control device 82 in the second ultrasonic diagnostic apparatus UL2 has the setting section 822, it does not have a converting section or a second transmitting section. Moreover, while the server control device 141 in the server 104 has the server transmitting section 1412, it does not have a converting section. The server control device 141 in the present embodiment is an exemplary embodiment of the server control device in the present invention.

Figure 18:
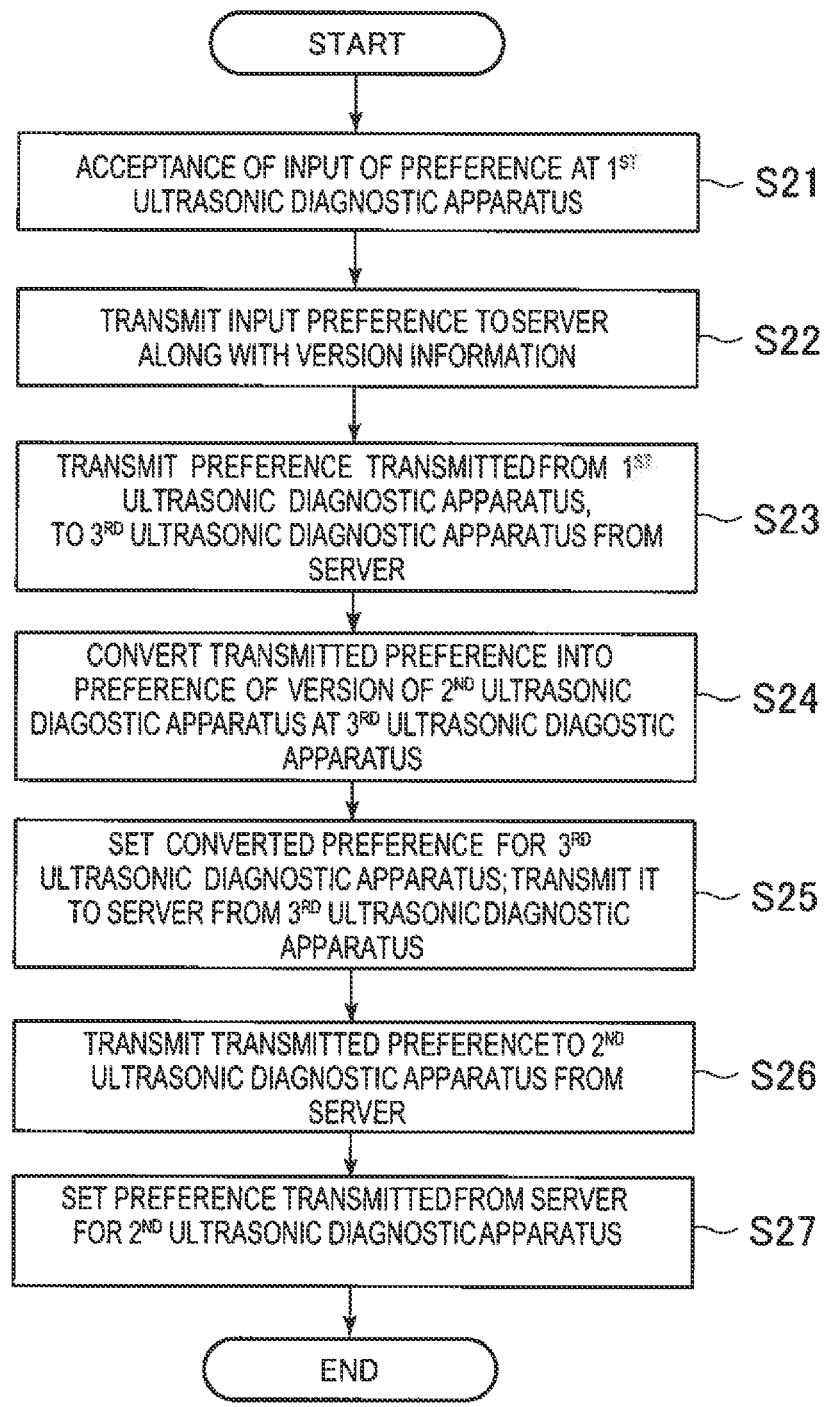
FIG. 18 is a flow chart showing an operation of the second variation of the first embodiment.

An operation of the second variation will be described based on the flow chart in FIG. 18. Steps S21, S22 are similar to Step S1, S2 in FIG. 4, description of which will be omitted. In the present embodiment, again, it is assumed that an input for selecting an image filter has been performed at the ultrasonic diagnostic apparatus 101.

At Step S23, the server transmitting section 1412 transmits the information of the preference and information representing version 2 transmitted at Step S22, to the third ultrasonic diagnostic apparatus UL3 via the network 105. The transmitting function of the server transmitting section 1412 is an exemplary embodiment of the output function executed by the server control device in the present invention.

Next, at Step S24, the information of the preference and information representing version 2 transmitted at Step S23 are input to the third ultrasonic diagnostic apparatus UL3. The third ultrasonic diagnostic apparatus UL3 is the ultrasonic diagnostic apparatus 102 in the latest version among the ultrasonic diagnostic apparatuses 101, 102, 103. The converting section 821 in the third ultrasonic diagnostic apparatus UL3 then performs conversion of the information of the preference input to the third ultrasonic diagnostic apparatus UL3. In the present variation, again, conversion from version 2 into versions 1 and 3 is performed, as in the first variation.

Figure 13:
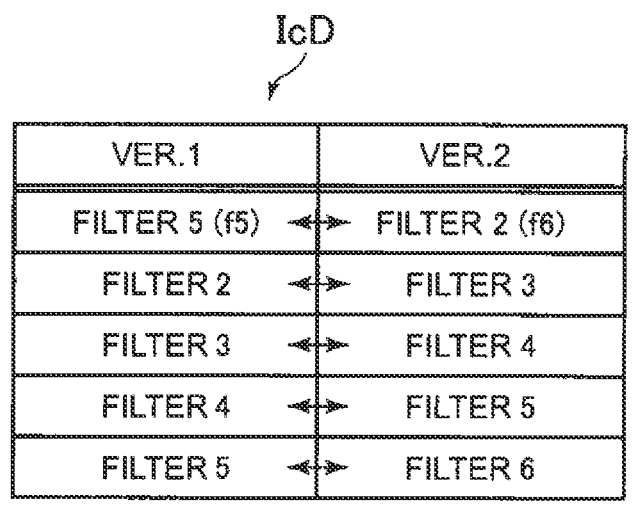
FIG. 13 is a diagram showing an example of conversion information in the first variation of the first embodiment.
Figure 14:
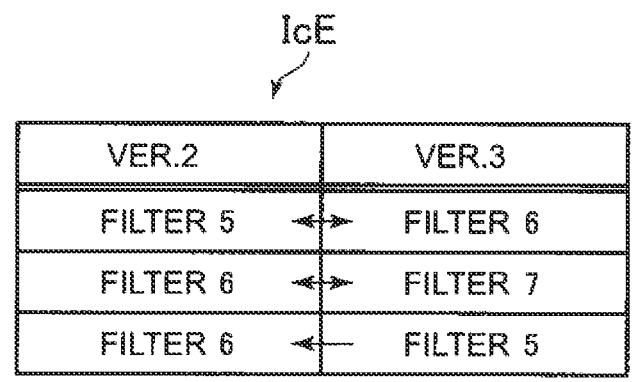
FIG. 14 is a diagram showing an example of the conversion information in the first variation of the first embodiment.
Figures 15, 16:
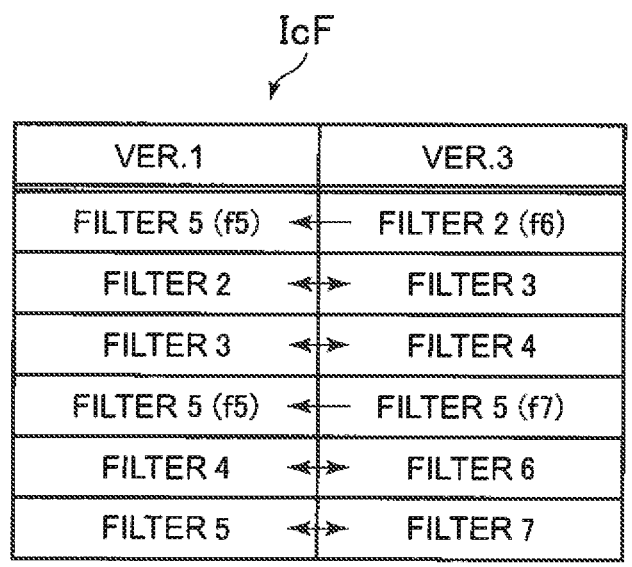
FIG. 15 is a diagram showing an example of the conversion information in the first variation of the first embodiment.
FIG. 16 is a diagram showing version information.

In the present variation, in the second storage device 92 in the ultrasonic diagnostic apparatus 102 serving as the third ultrasonic diagnostic apparatus UL3 are stored conversion information IcD to IcF described regarding the first variation and shown in FIG. 13 to FIG. 15. The converting section 821 performs conversion using the conversion information IcD, IcE, as in the first variation.

Here, the reason why the ultrasonic diagnostic apparatus 102 in the latest version serves as the third ultrasonic diagnostic apparatus UL3 is that the ultrasonic diagnostic apparatus 102 in the latest version is capable of carrying information on version-to-version conversion for all the ultrasonic diagnostic apparatuses in the system 100.

Next, at Step S25, the setting section 822 in the third ultrasonic diagnostic apparatus UL3 performs setting of the image filter by storing into the second storage device 92 "Image filter 7" and its mathematical function f5 converted from "Image filter 6" at Step S24 as the image filter to be used in the third ultrasonic diagnostic apparatus UL3. Moreover, the second transmitting section 823 in the third ultrasonic diagnostic apparatus UL3 transmits the information representing "Image filter 5" converted from "Image filter 6" at Step S24 to the server 104 via the network 105, along with its version information (version 1).

Next, at Step S26, the server transmitting section 1412 transmits to the second ultrasonic diagnostic apparatus UL2 via the network 105 the information representing "Image filter 5" transmitted from the third ultrasonic diagnostic apparatus UL3 at Step S25.

The server transmitting section 1412 identifies the second ultrasonic diagnostic apparatus UL2 that is the destination of transmission of the information representing "Image filter 5" based on the version identification information Iv, as in the first variation. More particularly, the server transmitting section 1412 identifies the second ultrasonic diagnostic apparatus UL2 that is the destination of transmission of the information representing "Image filter 5" as the ultrasonic diagnostic apparatus 103 based on the information representing version 1 transmitted from the third ultrasonic diagnostic apparatus UL3 at Step S25 and the version identification information Iv. The server transmitting section 1412 then transmits the information representing "Image filter 5" to the ultrasonic diagnostic apparatus 103 via the network 105.

Next, at Step S27, the setting section 822 in the ultrasonic diagnostic apparatus 103 serving as the second ultrasonic diagnostic apparatus UL2 performs setting of the image filter by storing into the second storage device 92 "Image filter 5" and its mathematical function f5 transmitted from the server 104 as the image filter to be used in the ultrasonic diagnostic apparatus 103.

Next, a second embodiment will be described. In the following description, details of similar matters to those in the first embodiment will be omitted.

Figure 19:
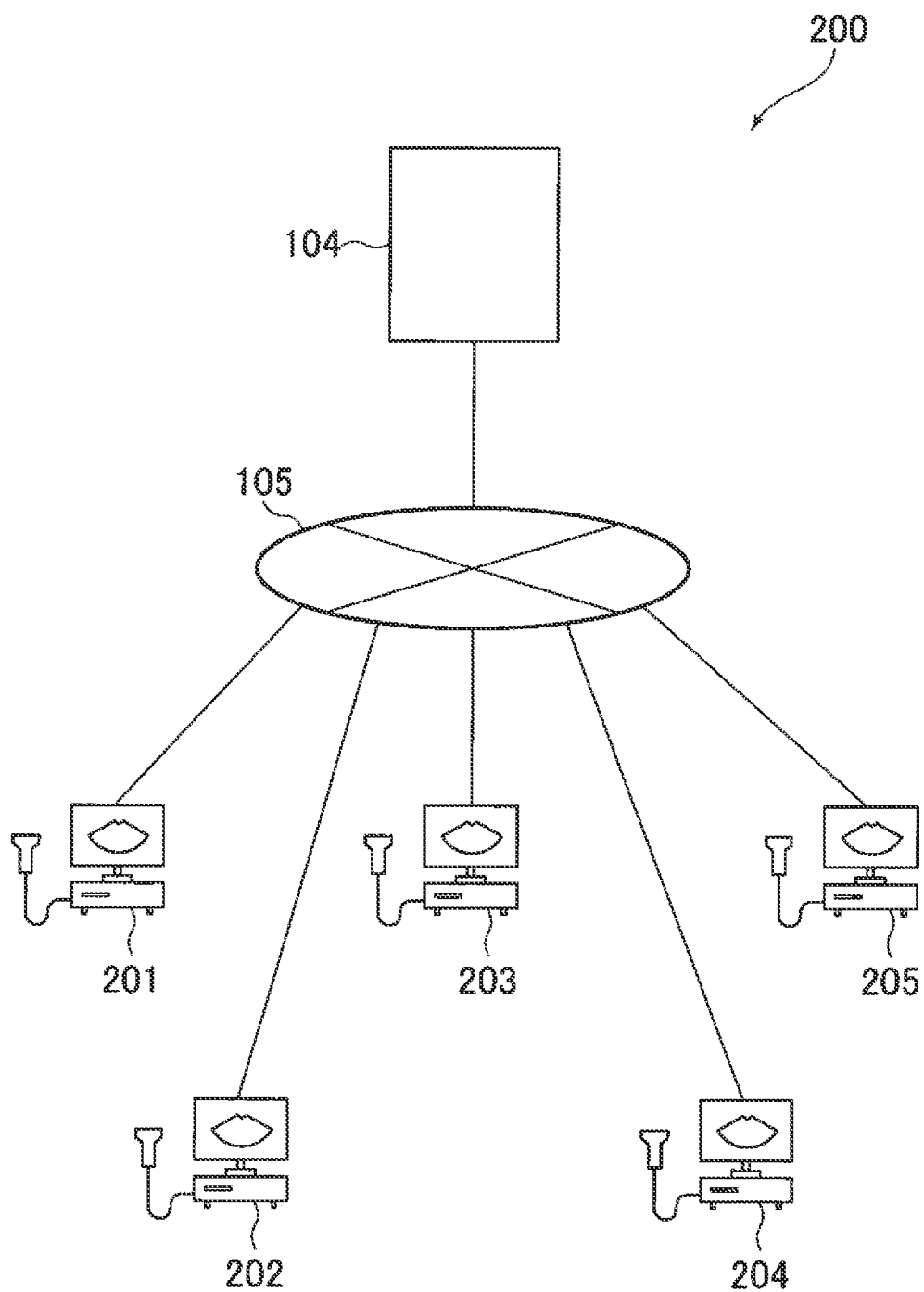
FIG. 19 is a block diagram showing the overall configuration of the system in a second embodiment of the present invention.

A system 200 in the present embodiment comprises ultrasonic diagnostic apparatuses 201, 202, 203, 204, 205, as shown in FIG. 19. Again, the ultrasonic diagnostic apparatuses 201, 202, 203, 204, 205 each have a configuration shown in FIG. 2, as in the ultrasonic diagnostic apparatuses 101, 102, 103.

Figure 20:
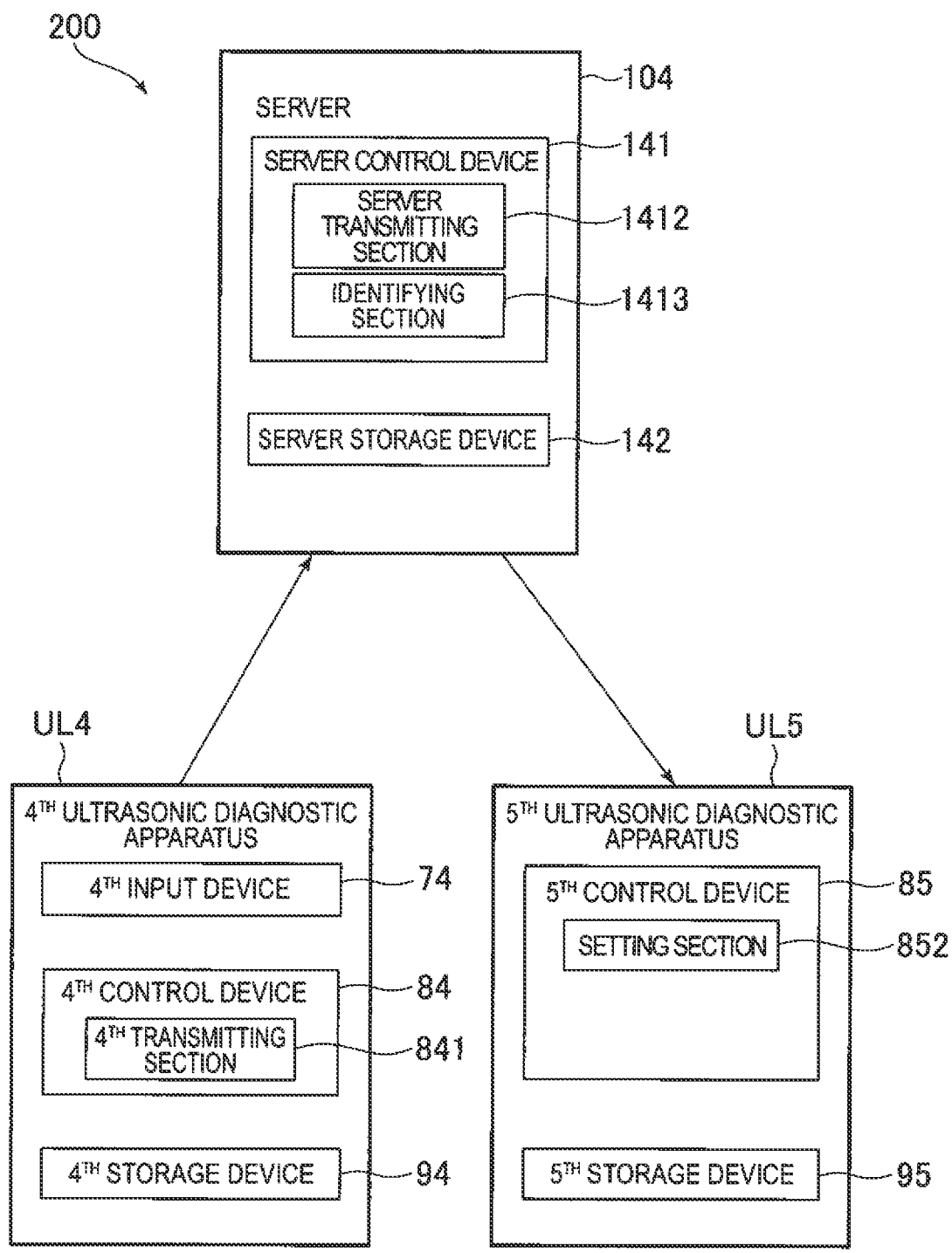
FIG. 20 is a block diagram showing a fourth ultrasonic diagnostic apparatus, a fifth ultrasonic diagnostic apparatus, and the server in the second embodiment.

In the present embodiment, the system 200 has a fourth ultrasonic diagnostic apparatus UL4 and a fifth ultrasonic diagnostic apparatus UL5, as shown in FIG. 20. In the present embodiment, the fourth ultrasonic diagnostic apparatus UL4 and fifth ultrasonic diagnostic apparatus UL5 are those of the plurality of ultrasonic diagnostic apparatuses 201, 202, 203, 204, 205 that share at least some preferences.

Similarly to the first embodiment, the fourth ultrasonic diagnostic apparatus UL4 is one of the plurality of ultrasonic diagnostic apparatuses 201, 202, 203, 204, 205 at which input of information of a preference is performed. The fifth ultrasonic diagnostic apparatus UL5 is an ultrasonic diagnostic apparatus into which the information of the preference input at the fourth ultrasonic diagnostic apparatus UL4 is set. Moreover, the fourth ultrasonic diagnostic apparatus UL4 and fifth ultrasonic diagnostic apparatus UL5 are those of the ultrasonic diagnostic apparatuses 201, 202, 203, 204, 205 that are of the same kind.

In the present embodiment, as shown in FIG. 21, the ultrasonic diagnostic apparatus 201 is in version 1 (Ver. 1), the ultrasonic diagnostic apparatus 202 is in version 2 (Ver. 2), and the ultrasonic diagnostic apparatus 203 is in version 3 (Ver. 3). The ultrasonic diagnostic apparatus 204 is in version 2 (Ver. 2), and the ultrasonic diagnostic apparatus 205 is in version 1 (Ver. 1). Therefore, the ultrasonic diagnostic apparatuses 201, 205 are ultrasonic diagnostic apparatuses of the same kind, between which at least some preferences are shared. Similarly, the ultrasonic diagnostic apparatuses 202, 204 are ultrasonic diagnostic apparatuses of the same kind, between which at least some preferences are shared. The system 200 in the present embodiment may be said to comprise ultrasonic diagnostic apparatuses of a plurality of kinds.

Version identification information Iv for identifying the version of the ultrasonic diagnostic apparatuses 201, 202, 203, 204, 205 shown in FIG. 21 is stored in the server storage device 142 in the server 104. The version identification information Iv in the present embodiment is an exemplary embodiment of the kind identification information for identifying a kind of each of the plurality of medical image capture apparatuses in the present invention.

In the present embodiment, image filters in each of versions 1, 2, 3 are similar to those in the first embodiment. That is, in the storage device 9 of the ultrasonic diagnostic apparatuses 201, 205 in version 1 is stored image filter information If1 shown in FIG. 5. In the storage device 9 of the ultrasonic diagnostic apparatuses 202, 204 in version 2 is stored the image filter information If2 shown in FIG. 6. In the storage device 9 of the ultrasonic diagnostic apparatus 203 in version 3 is stored the information on the image filter If3 shown in FIG. 7.

The input device 7, control device 8, and storage device 9 of the fourth ultrasonic diagnostic apparatus UL4 in the present embodiment will be referred to herein as a fourth input device 74, a fourth control device 84, and a fourth storage device 94, respectively, as shown in FIG. 20. The control device 8 and storage device 9 of the fifth ultrasonic diagnostic apparatus UL5 will be referred to herein as a fifth control device 85 and a fifth storage device 95, respectively, as shown in FIG. 20.

The fourth input device 74 is an exemplary embodiment of the input device in the present invention. The fourth control device 84 loads a program stored in the fourth storage device 94, and causes the function of the fourth transmitting section 841 to be executed according to the program. The function of the fourth transmitting section 841 will be discussed later. The function of the fourth transmitting section 841 is an exemplary embodiment of the fourth output function in the present invention. The fourth control device 84 is an exemplary embodiment of the fourth control device in the present invention.

The fifth control device 85 loads a program stored in the fifth storage device 95, and causes the function of the setting section 852 to be executed according to the program. The function of the setting section 852 will be discussed later. The function of setting section 852 is an exemplary embodiment of the setting function in the present invention. The fifth control device 85 is an exemplary embodiment of the fifth control device in the present invention.

In the present embodiment, the server control device 141 in the server 104 has a server transmitting section 1412 and an identifying section 1413. The functions of the server transmitting section 1412 and identifying section 1413 will be discussed later. The server control device 141 is an exemplary embodiment of the sixth control device in the present invention. The function of the server transmitting section 1412 is an exemplary embodiment of the sixth output function in the present invention. The function of the identifying section 1413 is an exemplary embodiment of the identifying function in the present invention.

Figure 22:
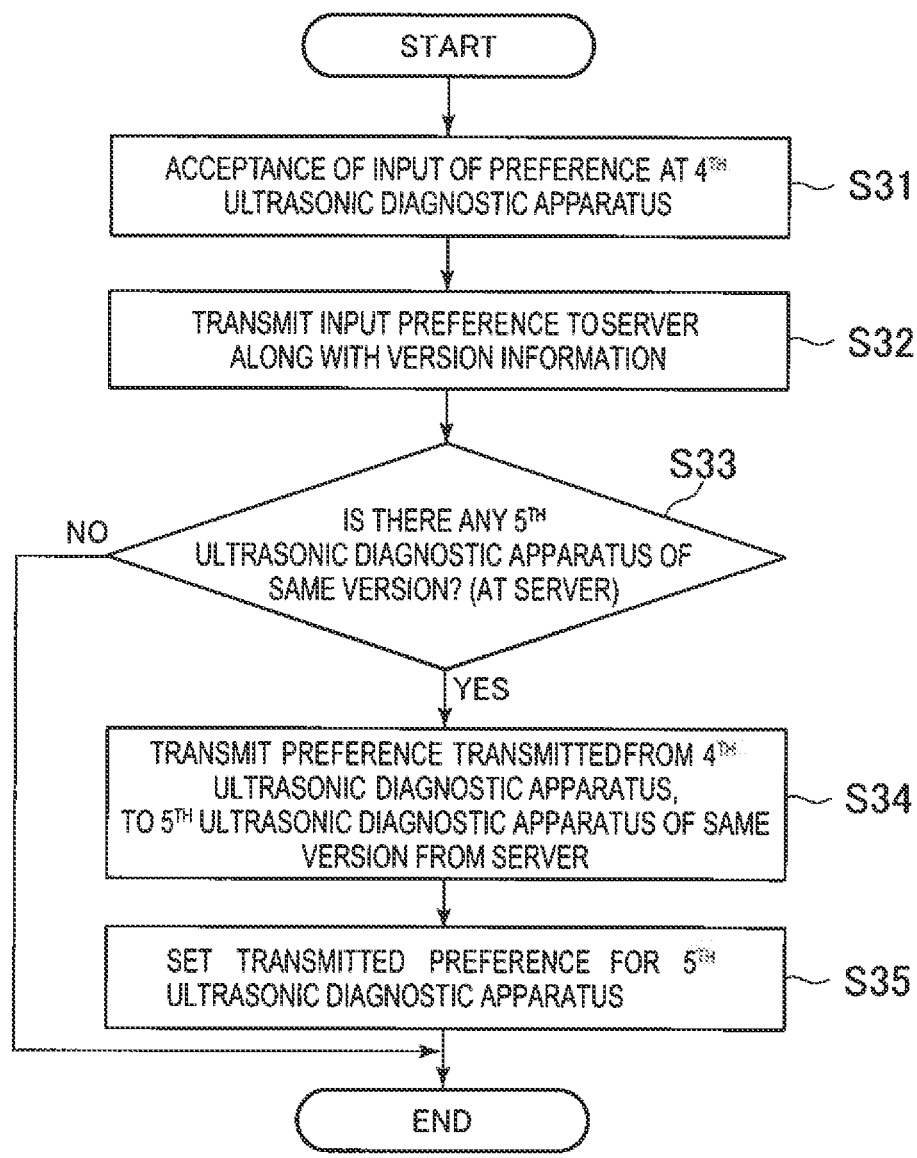
FIG. 22 is a flow chart showing an operation of the second embodiment.

Now an operation of the second embodiment will be described based on the flow chart in FIG. 22. First, at Step S31, the fourth input device 74 in the fourth ultrasonic diagnostic apparatus UL4 accepts an operator's input of information of a preference. The information of the preference input here is one to be shared among those of the ultrasonic diagnostic apparatuses 201, 202, 203, 204, 205 that have the same version. In the present embodiment, the first input device 74 accepts an input of selecting one of a plurality of image filters, as in the first embodiment. Similarly to the first embodiment, said input is accepted at the ultrasonic diagnostic apparatus 201. That is, the fourth ultrasonic diagnostic apparatus UL4 is the ultrasonic diagnostic apparatus 201.

Next, at Step S32, the fourth transmitting section 841 transmits information on the image filter input at Step S31 to the server 104 via the network 105. The fourth transmitting section 841 transmits said information on the image filter along with information representing the version (version 1) of the ultrasonic diagnostic apparatus 201 to said server 104, as in the first embodiment. The information on the image filter may be a filter name or a mathematical function.

At Step S33, the identifying section 1413 decides whether or not there exists in the system 200 any fifth ultrasonic diagnostic apparatus UL5 in the same version as that transmitted to the server 104 at Step S32. The identifying section 1413 makes the decision based on the version identification information Iv. Since information representing version 1 of the ultrasonic diagnostic apparatus 101 is transmitted at Step S32 in the present embodiment, the identifying section 1413 decides whether or not there exists an ultrasonic diagnostic apparatus in version 1, which is the same as the ultrasonic diagnostic apparatus 201, based on the version identification information Iv. Since the ultrasonic diagnostic apparatus 205 is in version 1 in the version identification information Iv in the present embodiment, the identifying section 1413 decides that there exists an ultrasonic diagnostic apparatus in version 1, which is the same as the ultrasonic diagnostic apparatus 201. The identifying section 1413 then identifies the ultrasonic diagnostic apparatus 205 as the fifth ultrasonic diagnostic apparatus UL5 in the same version as the ultrasonic diagnostic apparatus 201.

In the case that it is decided that there exists the fifth ultrasonic diagnostic apparatus UL5 in the same version at Step S33 ("YES" at Step S33), the flow moves to the processing at Step S34. On the other hand, in the case that it is decided that there exists no fifth ultrasonic diagnostic apparatus UL5 in the same version at Step S33 ("NO" at Step S33), the processing is terminated.

Since in the present embodiment, the identifying section 1413 decides that there exists an ultrasonic diagnostic apparatus in version 1 that is the same as the ultrasonic diagnostic apparatus 201, the flow goes to Step S34. At Step S34, the server transmitting section 1412 transmits the information on the image filter transmitted from the ultrasonic diagnostic apparatus 201, to the ultrasonic diagnostic apparatus 205 identified as the fifth ultrasonic diagnostic apparatus UL5 at Step S33.

Next, at Step 35, the setting section 852 sets the image filter transmitted from the server 104 as the image filter to be used in the ultrasonic diagnostic apparatus 205 serving as the fifth ultrasonic diagnostic apparatus UL5. The setting section 852 performs the setting of the image filter by storing the filter name and its mathematical function of the image filter into the fifth storage device 95.

According to the present embodiment described above, image filters are set for the fourth ultrasonic diagnostic apparatus UL4 and fifth ultrasonic diagnostic apparatus UL5 in the same version, and thus, a failure or an unexpected behavior of the apparatuses can be prevented from occurring.

Figure 23:
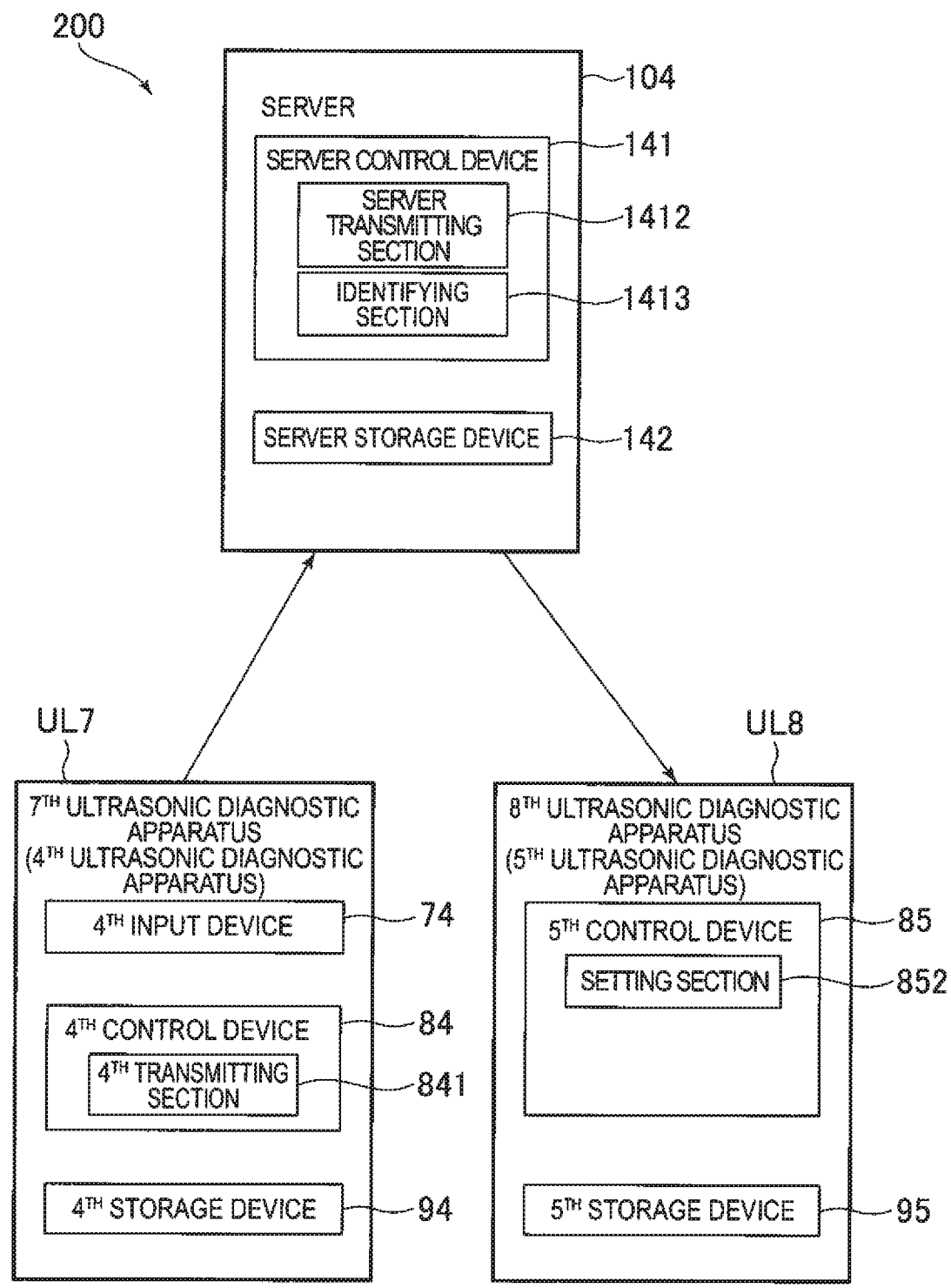
FIG. 23 is a block diagram showing a seventh ultrasonic diagnostic apparatus, an eighth ultrasonic diagnostic apparatus, and the server in a first variation of the second embodiment.

Next, variations of the second embodiment will be described. First, a first variation will be described. As shown in FIG. 23, the system 200 in the first variation has a seventh ultrasonic diagnostic apparatus UL7 and an eighth ultrasonic diagnostic apparatus UL8. In the present variation, the ultrasonic diagnostic apparatuses 201, 202 shown in FIG. 19 correspond to the seventh ultrasonic diagnostic apparatus UL7, and the ultrasonic diagnostic apparatus 204, 205 correspond to the eighth ultrasonic diagnostic apparatus UL8. That is, while in FIG. 23, the seventh ultrasonic diagnostic apparatus UL7 and eighth ultrasonic diagnostic apparatus UL8 are each shown to comprise one apparatus, the system 200 comprises a plurality of the seventh ultrasonic diagnostic apparatuses UL7 and a plurality of the eighth ultrasonic diagnostic apparatuses UL8.

Moreover, the ultrasonic diagnostic apparatuses 201, 202 are in mutually different versions, so that the plurality of seventh ultrasonic diagnostic apparatuses UL7 are of mutually different kinds. Similarly, the ultrasonic diagnostic apparatus 204, 205 are in mutually different versions, so that the plurality of eighth ultrasonic diagnostic apparatuses UL8 are of mutually different kinds.

Furthermore, the ultrasonic diagnostic apparatuses 201, 205 are of the same version, and the ultrasonic diagnostic apparatuses 202, 204 are of the same version, so that the system 200 comprises ultrasonic diagnostic apparatuses of the same kind between the seventh ultrasonic diagnostic apparatuses UL7 and eighth ultrasonic diagnostic apparatuses UL8. It is assumed here that the seventh ultrasonic diagnostic apparatus UL7 and eighth ultrasonic diagnostic apparatus UL8 shown in FIG. 23 are ultrasonic diagnostic apparatuses of the same version.

The seventh ultrasonic diagnostic apparatus UL7 has the fourth input device 74, fourth control device 84, and fourth storage device 94. The eighth ultrasonic diagnostic apparatus UL8 has the fifth control device 85 and fifth storage device 95.

Of the plurality of seventh ultrasonic diagnostic apparatuses UL7 and the plurality of eighth ultrasonic diagnostic apparatuses UL8, those sharing information of preferences constitute the fourth medical image capture apparatus UL4 and fifth medical image capture apparatus UL5.

Figure 24:
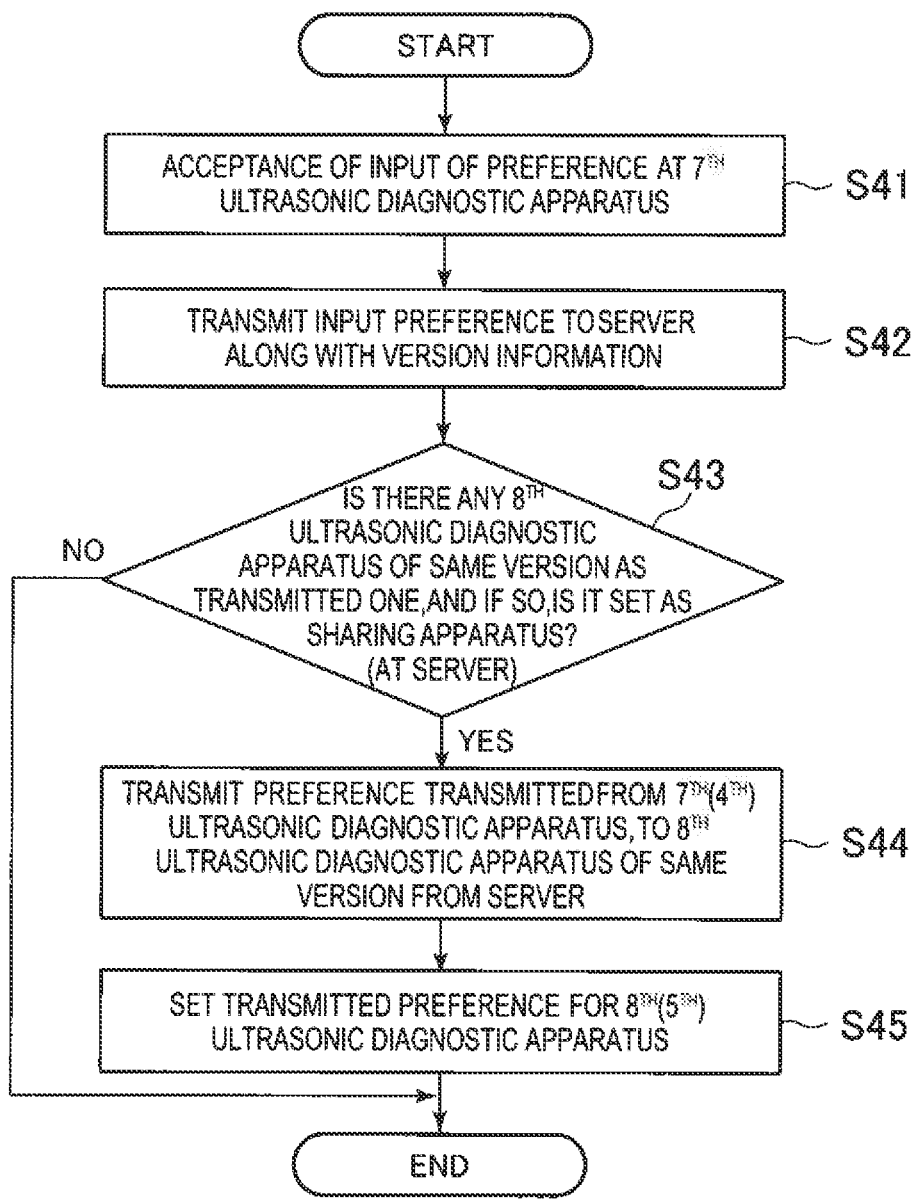
FIG. 24 is a flow chart showing an operation of the first variation of the second embodiment.

Now an operation of the present variation will be described based on the flow chart in FIG. 24. First, at Step S41, the fourth input device 74 in the seventh ultrasonic diagnostic apparatus UL7 accepts an operator's input of information of a preference. In the present variation, again, the fourth input device 74 accepts an input of selecting one of a plurality of image filters, as in Step S31 described above. Said input is accepted at the ultrasonic diagnostic apparatus 201, as in Step S31 described above.

At Step S42, similar processing to that at Step S32 is performed. In the present variation, however, information representing the version (version 1) of the ultrasonic diagnostic apparatus 201 is further transmitted to the server 104.

Next, at Step S43, the identifying section 1413 decides whether or not there exists in the system 200 any eighth ultrasonic diagnostic apparatus UL8 in the same version as that transmitted to the server 104 at Step S42, as in Step S33. At Step S42 in the present variation, the information representing version 1 of the ultrasonic diagnostic apparatus 201 is transmitted, so that the identifying section 1413 decides whether or not there exists any ultrasonic diagnostic apparatus in version 1 that is the same as the ultrasonic diagnostic apparatus 201 based on the identification information Iv shown in FIG. 21. Since in the version identification information Iv shown in FIG. 21, the ultrasonic diagnostic apparatus 205 is in version 1, the identifying section 1413 decides that there exists an ultrasonic diagnostic apparatus in version 1 that is the same as the ultrasonic diagnostic apparatus 201. The identifying section 1413 then identifies the ultrasonic diagnostic apparatus 205 as the eighth ultrasonic diagnostic apparatus UL8 in the same version as the ultrasonic diagnostic apparatus 201.

At Step S43, the identifying section 1413 decides whether or not the ultrasonic diagnostic apparatus in the version transmitted to the server 104 at Step S42 shares information of a preference. In the present variation, the identifying section 1413 decides whether or not the ultrasonic diagnostic apparatuses 201, 205 in version 1 share information of a preference between them. The identifying section 1413 makes the decision based on sharing apparatus identification information Id shown in FIG. 25. The sharing apparatus identification information Id is information for identifying ultrasonic diagnostic apparatuses in the same version among the ultrasonic diagnostic apparatuses 201, 202, 203, 204, 205 that share information of a preference, and their version. The sharing apparatus identification information Id is stored in the server storage device 142. The sharing apparatus identification information Id is an exemplary embodiment of the sharing apparatus identification information in the present invention.

In the sharing apparatus identification information Id in the present variation, the ultrasonic diagnostic apparatuses 201, 205 and their version, version 1, are identified as the ultrasonic diagnostic apparatuses between which information of a preference is shared, and as their version. Therefore, it is decided that information of a preference is shared at Step S43. In this case, the ultrasonic diagnostic apparatus 201 serving as the seventh ultrasonic diagnostic apparatus UL7 corresponds to the fourth ultrasonic diagnostic apparatus UL4. The ultrasonic diagnostic apparatus 205 serving as the eighth ultrasonic diagnostic apparatus UL8 corresponds to the fifth ultrasonic diagnostic apparatus UL5.

In the case that it is decided at Step S43 that there exists an eighth ultrasonic diagnostic apparatus UL8 in the same version, and information of a preference is shared therewith ("YES" at Step S43), the flow moves to the processing at Step S44. On the other hand, In the case that it is decided at Step S43 that there exists no eighth ultrasonic diagnostic apparatus UL8 in the same version, or information of a preference is not shared ("NO" at Step S43), the processing is terminated. For example, assuming that the input at Step S41 is performed at the ultrasonic diagnostic apparatus 202, version 2 of the ultrasonic diagnostic apparatus 202 does not share information of a preference in the sharing apparatus identification information Id, so that it is decided that the information of the preference is not shared.

At Step S44, the server transmitting section 1412 transmits to the ultrasonic diagnostic apparatus 205 the information on the image filter transmitted from the ultrasonic diagnostic apparatus 201. Next, at Step S45, the setting section 852 sets the image filter transmitted from the server 104 as the image filter to be used in the ultrasonic diagnostic apparatus 205. The setting section 852 performs the setting of the image filter by storing the image filter's filter name and its mathematical function into the fifth storage device 95.

Figure 26:
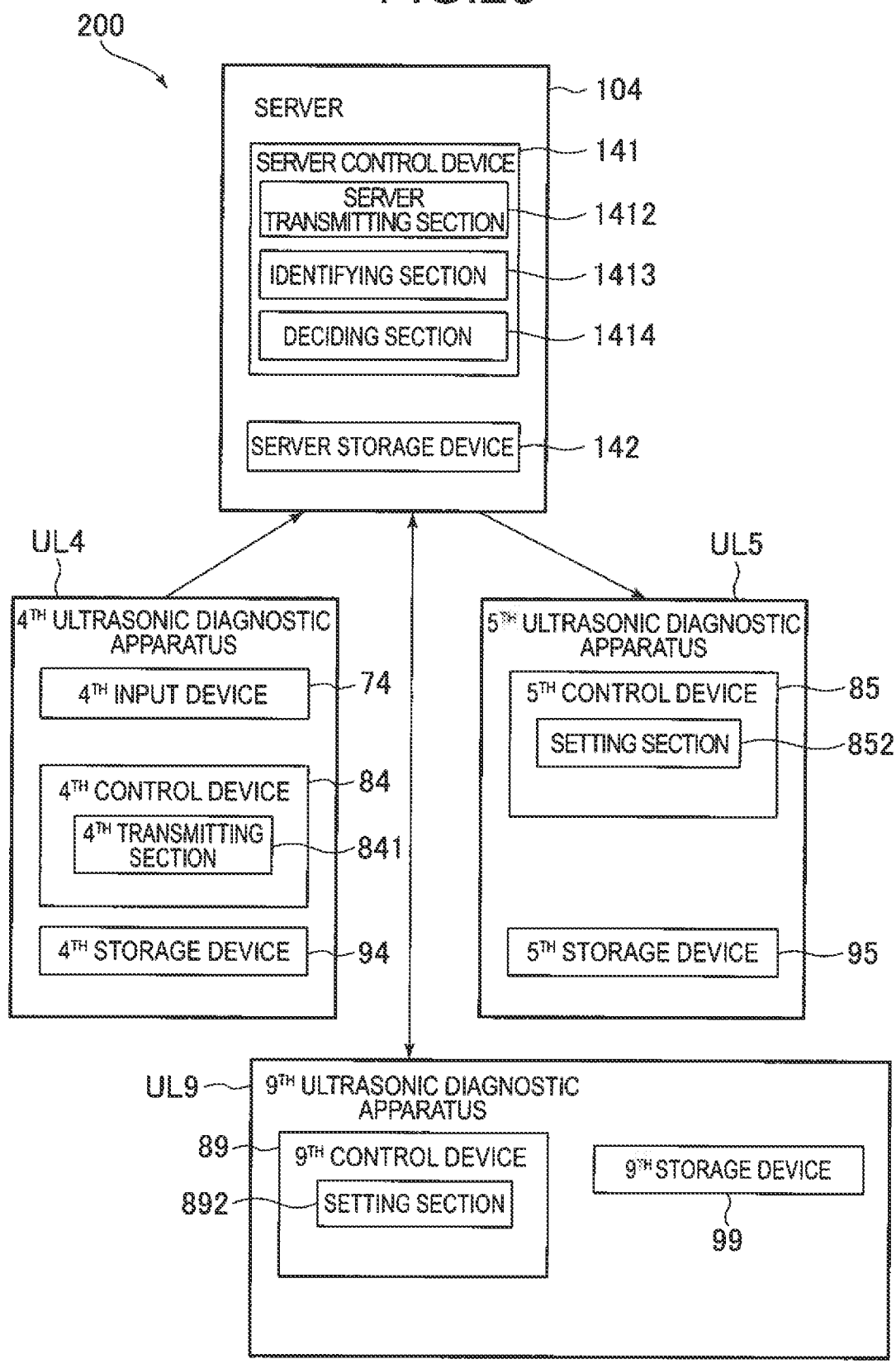
FIG. 26 is a block diagram showing the fourth ultrasonic diagnostic apparatus, fifth ultrasonic diagnostic apparatus, a ninth medical image capture apparatus, and the server in a second variation of the second embodiment.

Next, a second variation will be described. The system 200 in the second variation has a fourth ultrasonic diagnostic apparatus UL4, a fifth ultrasonic diagnostic apparatus UL5, a ninth medical image capture apparatus UL9, and a server 104, as shown in FIG. 26. In the present variation, again, the fourth ultrasonic diagnostic apparatus UL4 and fifth ultrasonic diagnostic apparatus UL5 are those of the plurality of ultrasonic diagnostic apparatuses 201, 202, 203, 204, 205 that are of the same kind and share at least some information.

For example, in the case that the ultrasonic diagnostic apparatus 201 serves as the fourth ultrasonic diagnostic apparatus UL4, the ultrasonic diagnostic apparatus 205 serves as the fifth ultrasonic diagnostic apparatus UL5. In the case that the ultrasonic diagnostic apparatus 202 serves as the fourth ultrasonic diagnostic apparatus UL4, the ultrasonic diagnostic apparatus 204 serves as the fifth ultrasonic diagnostic apparatus UL5. The ultrasonic diagnostic apparatuses 201, 205 are in version 1, and the ultrasonic diagnostic apparatuses 202, 204 are in version 2. Therefore, the system 200 comprises a plurality of ultrasonic diagnostic apparatuses of different kinds as the fourth ultrasonic diagnostic apparatuses UL4, and at the same time, a plurality of ultrasonic diagnostic apparatuses of different kinds as the fifth ultrasonic diagnostic apparatuses UL5.

The ninth ultrasonic diagnostic apparatus UL9 is one of the plurality of ultrasonic diagnostic apparatuses 201, 202, 203, 204, 205 that is of a kind different from that of the fourth ultrasonic diagnostic apparatus UL4 and fifth ultrasonic diagnostic apparatus UL5. In the present variation, the ninth ultrasonic diagnostic apparatus UL9 is in a version different from those of the fourth ultrasonic diagnostic apparatus UL4 and fifth ultrasonic diagnostic apparatus UL5. For example, in the case that the ultrasonic diagnostic apparatus 201 serves as the fourth ultrasonic diagnostic apparatus UL4, the ultrasonic diagnostic apparatuses 202, 203, 204 serve as the ninth ultrasonic diagnostic apparatuses UL9. In the case that the ultrasonic diagnostic apparatus 202 serves as the fourth ultrasonic diagnostic apparatus UL4, the ultrasonic diagnostic apparatuses 201, 203, 205 serve as the ninth ultrasonic diagnostic apparatuses UL9.

In the present variation, information which is shared between the fourth and fifth medical image capture apparatuses UL4 and UL5, and the ninth medical image capture apparatus UL9 will be referred to herein as first information. Moreover, information which is shared solely between the fourth medical image capture apparatus UL4 and fifth medical image capture apparatus UL5 will be referred to herein as second information.

The control device 8 and storage device 9 in the ninth ultrasonic diagnostic apparatus UL9 are designated herein as a ninth control device 89 and a ninth storage device 99. The ninth control device 89 is an exemplary embodiment of the ninth control device in the present invention.

In the present variation, the server control device 141 in the server 104 has a deciding section 1414, in addition to the server transmitting section 1412 and identifying section 1413. The function of the deciding section 1414 is an exemplary embodiment of the deciding function in the present invention.

Figure 27:
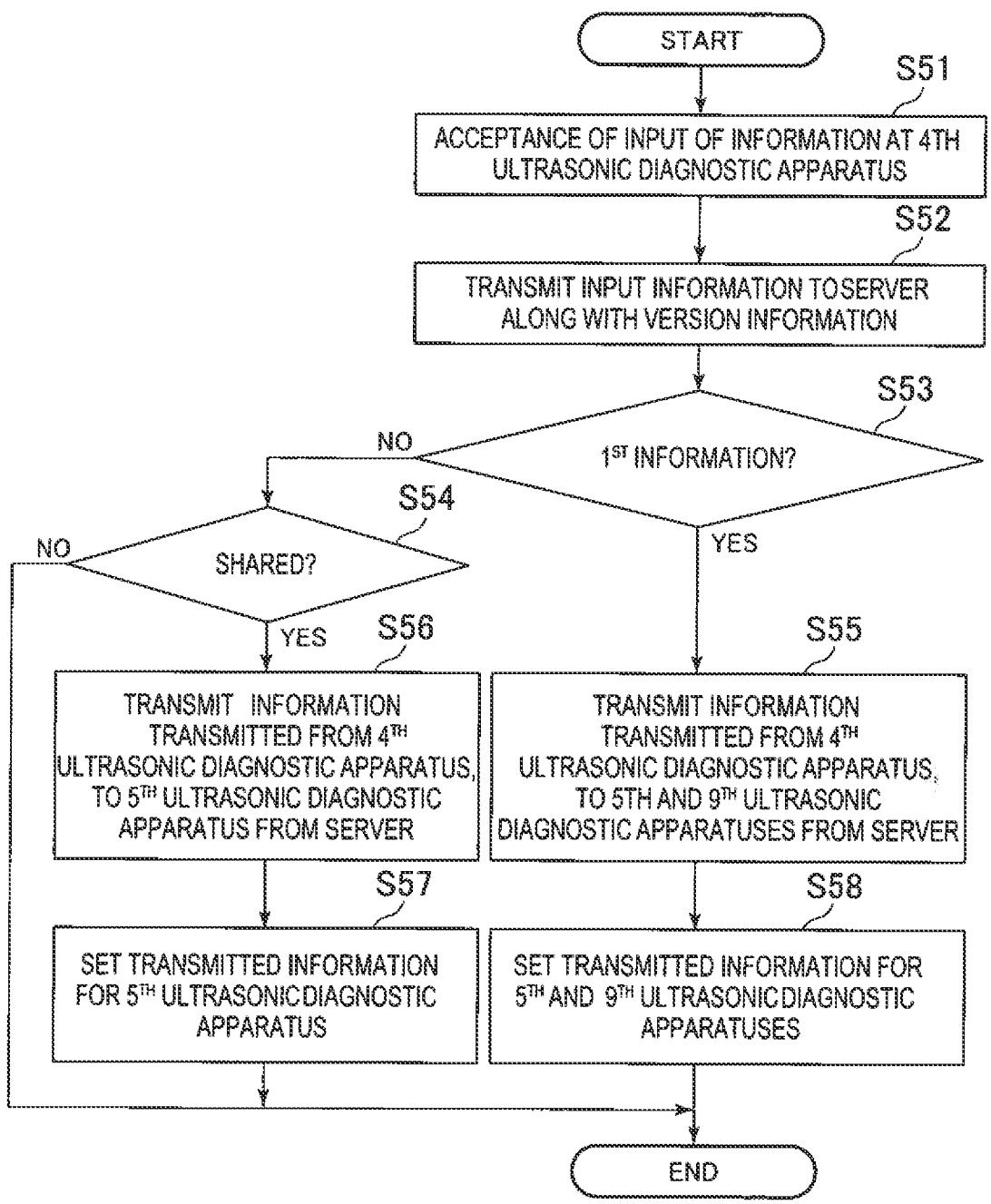
FIG. 27 is a flow chart showing an operation of the second variation of the second embodiment.

Now an operation of the second variation will be described based on the flow chart in FIG. 27. First, at Step S51, the fourth input device 74 in the fourth ultrasonic diagnostic apparatus UL4 accepts an operator's input of information. In the present variation, it is assumed that the fourth ultrasonic diagnostic apparatus UL4 is any one of the ultrasonic diagnostic apparatuses 201, 202, 204, 205.

Assume that the information input in the present variation is any information A, B or C, which will be discussed later. Note that information A, B, C are merely exemplary, and the information in the present invention is not limited thereto.

Next, at Step S52, the fourth transmitting section 841 transmits to the server 104 via the network 105 the information input at Step S51. The fourth transmitting section 841 transmits the information to said server 104 along with information representing the version of the fourth ultrasonic diagnostic apparatus UL4 at which input has been performed at Step S51.

Figure 28:
FIG. 28 is a diagram showing an example of preference identification information.

Next, at Step S53, the deciding section 1414 decides whether or not the information transmitted to the server 104 at Step S52 matches the first information. The deciding section 1414 makes the decision based on the identification information Ii shown in FIG. 28.

The identification information Ii is stored in the server storage device 142, and it identifies information A, B, C as the first information or the second information. Specifically, information A is information to be shared among ultrasonic diagnostic apparatuses in all versions, i.e., among the fourth ultrasonic diagnostic apparatus(es) UL4, fifth ultrasonic diagnostic apparatus(es) UL5, and ninth ultrasonic diagnostic apparatus(es) UL9, which matches the first information.

On the other hand, information B, C each match the second information. Information B is information to be shared among all ultrasonic diagnostic apparatuses in the same version, i.e., among all the fourth ultrasonic diagnostic apparatus(es) UL4 and fifth ultrasonic diagnostic apparatus(es) UL5. Information C is information to be shared among the fourth ultrasonic diagnostic apparatus(es) UL4 and fifth ultrasonic diagnostic apparatus(es) UL5 in version 1. Therefore, information C is information to be shared among those of all the fourth ultrasonic diagnostic apparatus(es) UL4 and fifth ultrasonic diagnostic apparatus(es) UL5 that are in part of the versions.

Here, some information is compatible among ultrasonic diagnostic apparatuses of different kinds, such as the version, and can be harmlessly shared among them, and other information is harmful when it's shared across ultrasonic diagnostic apparatuses of different kinds because they have different values across them. For example, in some cases, values of preferences for image quality setting, which is one example of the information, are different across ultrasonic diagnostic apparatuses of different kinds; in other cases, information for performing measurement, which is other example of the information, is the same among ultrasonic diagnostic apparatuses of different kinds. The aforementioned first information is information that can be harmlessly shared among ultrasonic diagnostic apparatuses of different kinds. The aforementioned second information is information that is harmful when it is shared across ultrasonic diagnostic apparatuses of different kinds.

In the case that the information transmitted to the server 104 at Step S52 matches the second information, the deciding section 1414 decides that it does not match the first information ("NO" at Step S53). In this case, the flow moves to the processing at Step S54. On the other hand, in the case that it is decided by the deciding section 1414 that the information transmitted to the server 104 at Step S52 matches the first information ("YES" at Step S53), the flow moves to the processing at Step S55.

At Step S54, the deciding section 1414 decides whether or not there exists any ultrasonic diagnostic apparatus in the same version as that transmitted to the server 104 at Step S52 based on the version identification information Iv (see FIG. 21). The deciding section 1414 also decides whether or not the version and the information transmitted to the server 104 at Step S52 are those to be shared among the fourth ultrasonic diagnostic apparatus(es) UL4 and fifth ultrasonic diagnostic apparatus(es) UL5 based on the identification information Ii. For example, the information transmitted at Step S52 is information B or C and version information transmitted at Step S52 is version 1, the deciding section 1414 decides that they are the version and information to be shared. In the case that it is decided that the version and information are to be shared, and at the same time, it is decided that there exists an ultrasonic diagnostic apparatus in the same version ("YES" at Step S54), the flow moves to the processing at Step S56.

On the other hand, in the case that there exists no ultrasonic diagnostic apparatus in the same version as that transmitted to the server 104 at Step S52 or it is decided that the version and the information transmitted to the server 104 at Step S52 are not a version and information to be shared among the fourth ultrasonic diagnostic apparatus(es) UL4 and fifth ultrasonic diagnostic apparatus(es) UL5 (Step S54 "NO" at), the processing is terminated. For example, assuming that information C is input at the ultrasonic diagnostic apparatus 202 in version 2 at Step S51, it is decided by the deciding section 1414 that they are not a version and information to be shared.

Next, at Step S56, the server transmitting section 1412 transmits to the fifth ultrasonic diagnostic apparatus UL5 the information (second information) transmitted from the fourth ultrasonic diagnostic apparatus UL4 at Step S52. Next, at Step S57, the setting section 852 sets the information transmitted from the server 104 into the fifth ultrasonic diagnostic apparatus UL5 by storing it into the fifth storage device 95.

In the case that it is decided in the processing at Step S53 that the information transmitted to the server 104 at Step S52 matches the first information, and the flow goes to the processing at Step S55, the server transmitting section 1412 transmits to the fifth ultrasonic diagnostic apparatus UL5 and ninth ultrasonic diagnostic apparatus UL9 at Step S55 the information (first information) transmitted from the fourth ultrasonic diagnostic apparatus UL4 at Step S52. Next, at Step S58, the setting section 852 sets the information transmitted from the server 104 into the fifth ultrasonic diagnostic apparatus UL5 by storing it into the fifth storage device 95. The setting section 892 also sets the information in transmitted from the server 104 into the ninth ultrasonic diagnostic apparatus UL9 by storing it into the ninth storage device 99.

While the present invention has been described with reference to the embodiments above, it will be easily recognized that the present invention may be practiced with several modifications without departing from the scope and spirit thereof. While in the embodiments above the preference or the information is exemplified by the image filter, the preference or the information in the present invention may be another imaging condition. Moreover, the preference or the information in the present invention may be one other than imaging conditions.

Furthermore, while in the first embodiment the information of the preference input at the first ultrasonic diagnostic apparatus UL1 at Step S3 is converted into information of the preference in the oldest one of the versions of the second ultrasonic diagnostic apparatus(es) UL2, the present invention is not limited thereto. For example, the information of the preference input at the first ultrasonic diagnostic apparatus UL1 at Step S3 may be converted into different information (referred to hereinbelow as independent information) from that in the second ultrasonic diagnostic apparatus UL2. In this case, at Step S5, conversion from the independent information into information of the preference in the second ultrasonic diagnostic apparatus UL2 is performed, and the information after the conversion is set into the second ultrasonic diagnostic apparatus UL2. Moreover, information on conversion from information of a preference in the first ultrasonic diagnostic apparatus UL1 into independent information is stored in the server storage device 142, and information on conversion from the independent information into information of a preference in the second ultrasonic diagnostic apparatus UL2 is stored in the second storage device 92. The independent information is an exemplary embodiment of the third information in the present invention.

This written description uses examples to disclose the present invention, including the best mode, and also to enable any person skilled in the art to practice the present invention, including making and using any computing system or systems and performing any incorporated methods. The patentable scope of the present invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system comprising:
   a first medical image capture apparatus and a second medical image capture apparatus connected via a network, said first medical image capture apparatus and said second medical image capture apparatus sharing information of at least some of a plurality of preferences set in each of said first and second medical image capture apparatuses, wherein said first and second medical image capture apparatuses are of different kinds, wherein the kind comprises at least one of a version type or a device type;
   a storage device;
   a first control device; and
   a second control device:
   wherein:
      said first medical image capture apparatus has an input device for accepting an input of information of a preference to be shared with said second medical image capture apparatus;
      said first control device is configured to output the information of said preference accepted by said input device to said network along with information on the kind of said first medical image capture apparatus;
      said storage device is configured to store conversion information for converting information of a preference in the kind of said first medical image capture apparatus into a preference in the kind of said second medical image capture apparatus, said conversion information being stored according to the kinds of said first and second medical image capture apparatuses; and
      said second control device is configured to:
         convert the information of said preference output by said first control device into the preference in the kind of said second medical image capture apparatus based on the conversion information, wherein said conversion information is identified by said information on the kind of said first medical image capture apparatus output by said first control device; and
         set the information of said preference, after being converted, into said second medical image capture apparatus.

2. The system as recited in claim 1, comprising:
   a server connected with said first and second medical image capture apparatuses via said network, wherein
   said first control device outputs the information of said preference and the information on said kind to said server via said network,
   said storage device and said second control device are provided in both said server and said second medical image capture apparatus,
   said conversion information is constructed to include first conversion information and second conversion information,
   said first conversion information is information for converting information of a preference in the kind of said first medical image capture apparatus into third information, and is stored in said storage device in said server according to the kind of said first medical image capture apparatus, said second conversion information is information for converting said third information into information of a preference in the kind of said second medical image capture apparatus, and is stored in said storage device in said second medical image capture apparatus according to the kind of said second medical image capture apparatus, and said second control device in said server converts the information of said preference output by said first medical image capture apparatus into said third information based on said first conversion information, and said second control device in said second medical image capture apparatus converts said third information into information of the preference in said second medical image capture apparatus based on said second conversion information.

3. The system as recited in claim 2, wherein:

said second medical image capture apparatus includes medical image capture apparatuses of a plurality of kinds, and said third information is information of a preference in a second medical image capture apparatus of any one of said plurality of kinds.

4. The system as recited in claim 2, wherein: said third information is not information on the kind of said second medical image capture apparatus.

5. The system as recited in claim 1, comprising:

a server connected with said first and second medical image capture apparatuses via said network, wherein said first control device outputs the information of said preference and the information on said kind to said server via said network, said storage device and said second control device are provided in said server, wherein the storage device provided in said server is further configured to store kind identification information for identifying the kind of said second medical image capture apparatus, and said second control device further transmits the information of the preference in the kind of said second medical image capture apparatus to said second medical image capture apparatus corresponding to said kind via said network based on the information on said kind.

6. The system as recited in claim 1, wherein:

said second medical image capture apparatus is configured to include a third medical image capture apparatus having said storage device and said second control device, and said second control device further transmits the information of the preference in the kind of said second medical image capture apparatus to said second medical image capture apparatus corresponding to said kind via said network.

7. The system as recited in claim 6, comprising:

a server connected with said first medical image capture apparatus, said second medical image capture apparatus, and said third medical image capture apparatus via said network, wherein said first control device outputs the information of said preference and the information on said kind to said server via said network, said server comprises a server control device outputting the information of said preference and the information on said kind to said third medical image capture apparatus via said network, and said second control device performs conversion on the information of said preference output by the output function by said server control device.

8. The system as recited in claim 7, wherein: said second control device transmits the information of the preference in the kind of said second medical image capture apparatus to the second medical image capture apparatus corresponding to said kind via said network and said server.

9. The system as recited in claim 1, wherein:

the information of said preference includes a formal information and a substantial information, said conversion information is information for converting the formal information of said preference in the kind of said first medical image capture apparatus into said preference in the kind of said second medical image capture apparatus, and the information of said preference converted by said converting function is said formal information.

10. The system as recited in claim 1, wherein:

the information of said preference includes a formal information and a substantial information, said conversion information is information for converting the substantial information of said preference in the kind of said first medical image capture apparatus into said preference in the kind of said second medical image capture apparatus, and the information of said preference converted by said converting function is said substantial information.

11. The system as recited in claim 1, wherein: said information includes imaging conditions in said medical image capture apparatuses.

12. The system as recited in claim 5, wherein: said information includes imaging conditions in said medical image capture apparatuses.

13. The system as recited in claim 6, wherein: said information includes imaging conditions in said medical image capture apparatuses.

* * * * *